(12) United States Patent
Tesar et al.

(10) Patent No.: US 9,803,191 B2
(45) Date of Patent: Oct. 31, 2017

(54) EXPRESSION AND SECRETION SYSTEM

(71) Applicant: Genentech, Inc., South San Francisco, CA (US)

(72) Inventors: Devin Tesar, San Bruno, CA (US); Xiaocheng Chen, Foster City, CA (US); Mark Dennis, San Carlos, CA (US); Isidro Hotzel, Brisbane, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/934,570

(22) Filed: Jul. 3, 2013

(65) Prior Publication Data

US 2014/0011981 A1    Jan. 9, 2014

Related U.S. Application Data

(60) Provisional application No. 61/668,397, filed on Jul. 5, 2012, provisional application No. 61/852,483, filed on Mar. 15, 2013, provisional application No. 61/819,063, filed on May 3, 2013.

(51) Int. Cl.
| | |
|---|---|
| *C12N 15/10* | (2006.01) |
| *C12N 15/74* | (2006.01) |
| *C12N 15/70* | (2006.01) |
| *C07K 16/00* | (2006.01) |
| *C12N 15/85* | (2006.01) |
| *C12P 21/02* | (2006.01) |

(52) U.S. Cl.
CPC .......... *C12N 15/1037* (2013.01); *C07K 16/00* (2013.01); *C12N 15/70* (2013.01); *C12N 15/74* (2013.01); *C12N 15/85* (2013.01); *C12P 21/02* (2013.01); *C07K 2319/02* (2013.01); *C07K 2319/40* (2013.01); *C07K 2319/735* (2013.01); *C12N 2820/10* (2013.01); *C12N 2820/55* (2013.01); *C12N 2820/85* (2013.01); *C12N 2830/42* (2013.01); *C12N 2830/55* (2013.01); *C12N 2830/85* (2013.01)

(58) Field of Classification Search
None
See application file for complete search history.

(56) References Cited

U.S. PATENT DOCUMENTS

| | | | |
|---|---|---|---|
| 5,561,053 A * | 10/1996 | Crowley | ............ C07K 14/7151 435/320.1 |
| 7,094,579 B2 | 8/2006 | Gray et al. | |
| 7,112,439 B2 | 9/2006 | Johnson et al. | |
| 7,906,327 B2 | 3/2011 | Johnson et al. | |
| 7,972,811 B2 | 7/2011 | Gray et al. | |
| 7,977,068 B2 | 7/2011 | Gray et al. | |

FOREIGN PATENT DOCUMENTS

| | | |
|---|---|---|
| EP | 2060628 B1 | 11/2011 |
| JP | 2009-535063 A | 10/2009 |
| WO | WO-01/00814 A2 | 1/2001 |
| WO | WO-02/02746 A2 | 1/2002 |
| WO | WO-03/031611 A2 | 4/2003 |
| WO | 03/068956 A1 | 8/2003 |
| WO | 2004/063343 A2 | 7/2004 |
| WO | WO-2009/111183 A1 | 9/2009 |
| WO | WO-2011/090762 A1 | 7/2011 |

OTHER PUBLICATIONS

Tesar et al. (Protein Engineering, Design and Selection 26:655-662 (2013)).*
Ibragimova and Eade (Biophysical Journal, Oct. 1999, vol. 77, pp. 2191-2198).*
Nagano et al. Biochem Biophys Res Commun 447; 655-659 (2014).*
Humphreys et al., "High-level periplasmic expression in *Escherichia coli* using a eukaryotic signal peptide: importance of codon usage at the 5' end of the coding sequence," Protein Expr Purif. 20(2):252-64 (2000).
Wang et al., "Adapter-directed display: a modular design for shuttling display on phage surfaces," J Mol Biol. 395(5):1088-101 (2010).
(UniProtKB:accession BIA4G9).
(UniProtKB:accession P15703).
(UniProtKB:accession P20029).
(UniProtKB:accession Q9BLZ2).
Baek et al., "An improved helper phage system for efficient isolation of specific antibody molecules in phage display" Nucleic Acids Res. 30(5):e18 (9 pages) ( 2002).
Choi et al., "Ex12 helper phage improves the quality of a phage-displayed antibody library by ameliorating the adverse effect of clonal variations" BMB Rep. 44(4):244-9 ( 2011).
Haas et al., "Immunoglobulin heavy chain binding protein" Nature 306(5941):387-9 ( 1983).
Hall et al., "Eukaryotic and prokaryotic signal peptides direct secretion of a bacterial endoglucanase by mammalian cells" J Biol Chem. 265(32):19996-9 ( 1990).
Humphreys et al., "High-level periplasmic expression in *Escherichia coli* using a eukaryotic signal peptide: importance of codon usage at the 5' end of the coding sequence" Protein Expr Purif. 20(2):252-64 ( 2000).
Johansson et al., "Efficient Expression of Recombinant Human Monoclonal Antibodies in Drosophila S2 Cells" Journal of Immunological Methods 31 8:37-46 ( 2007).
Kramer et al., "A novel helper phage that improves phage display selection efficiency by preventing the amplification of phages without recombinant protein" Nucleic Acids Res. 1131(11):e59 (9 pages) ( 2003).
Lee et al., "High-affinity human antibodies from phage-displayed synthetic Fab libraries with a single framework scaffold" J Mol Biol 340(5):1073-1093 ( 2004).

(Continued)

*Primary Examiner* — Peter J Reddig
(74) *Attorney, Agent, or Firm* — Clark & Elbing LLP; Karen L. Elbing

(57) ABSTRACT

The invention provides an expression and secretion system, and methods of using the same, for the expression and secretion of one fusion protein in prokaryotic cells and a second fusion protein in eukaryotic cells. Also provided herein are nucleic acid molecules, vectors and host cells comprising such vectors and nucleic acid molecules.

39 Claims, 13 Drawing Sheets

(56) References Cited

OTHER PUBLICATIONS

Mazor et al., "Isolation of engineered, full-length antibodies from libraries expressed in *Escherichia coli*" Nature Biotechnology 25(5):563-565 (May 2007).
McCafferty et al., "Phage Antibodies: Filamentous Phage Displaying Antibody Variable Domains" Nature 348:552-554 (Dec. 1990).
Munro et al., "An Hsp70-like protein in the ER: identity with the 78 kd glucose-regulated protein and immunoglobulin heavy chain binding protein" Cell 46(2):291-300 ( 1986).
Oh et al., "Enhancing phage display of antibody fragments using gIII-amber suppression" Gene 386(1-2):81-9 ( 2007).
Rakonjac et al,, "Filamentous phage infection-mediated gene expression: construction and propagation of the gIII deletion mutant helper phage R408d3" Gene 198(1-2):99-103 ( 1997).
Rondot et al., "A helper phage to improve single-chain antibody presentation in phage display" Nat Biotechnol 19:75-78 ( 2001).
Sidhu, "Phage display in pharmaceutical biotechnology" Curr Opin Biotech 11(6):610-616 ( 2000).
Smith, "Filamentous fusion phage: novel expression vectors that display cloned antigens on the virion surface" Science 228(4705):1315-1317 ( 1985).
Stephens et al., "Features of spliceosome evolution and function inferred from an analysis of the information at human splice sites" J Mol Biol. 228(4):1124-36 ( 1992).
Kozutsumi et al., "Identification of immunoglobulin heavy chain binding protein as glucose-regulated protein 78 on the basis of amino acid sequence, immunological cross-reactivity, and functional activity," J Cell Sci Suppl. 11:115-37 (1989).
Normington et al., "*S. cerevisiae* encodes an essential protein homologous in sequence and function to mammalian BiP," Cell. 57(7):1223-36 (1989).
Soltes et al., "On the influence of vector design on antibody phage display," J Biotechnol. 127(4):626-37 (2007) (16 pages).
Database Accession No. B1A4G6, retrieved Jun. 29, 2016 (7 pages).

\* cited by examiner

Natural Donor (intron1):   T  G  G  T  G  A  G  A
Consensus 5' Splice Donor: A  G  G  T  A  A  G  T
Donor1:                    A  G  G  T  A  A  G  A
*FIG. 5A*
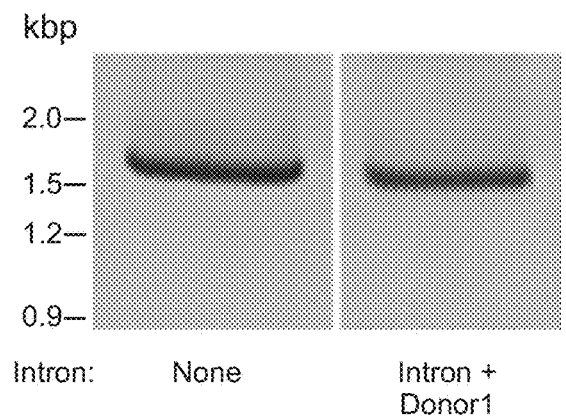
*FIG. 5B*
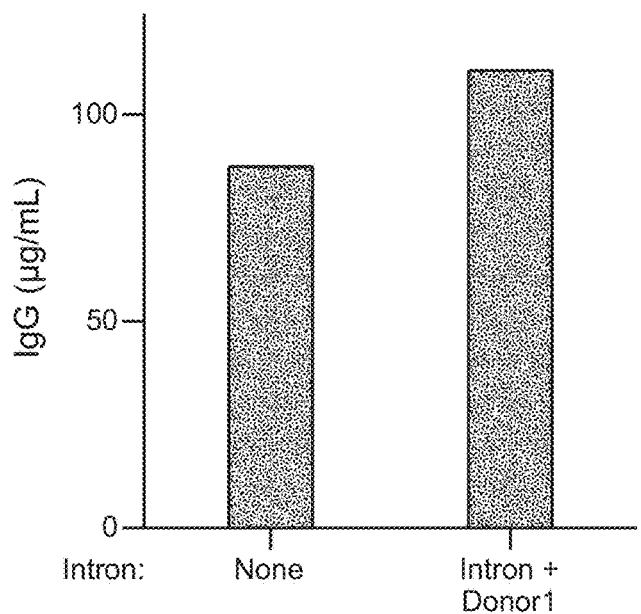
*FIG. 5C*

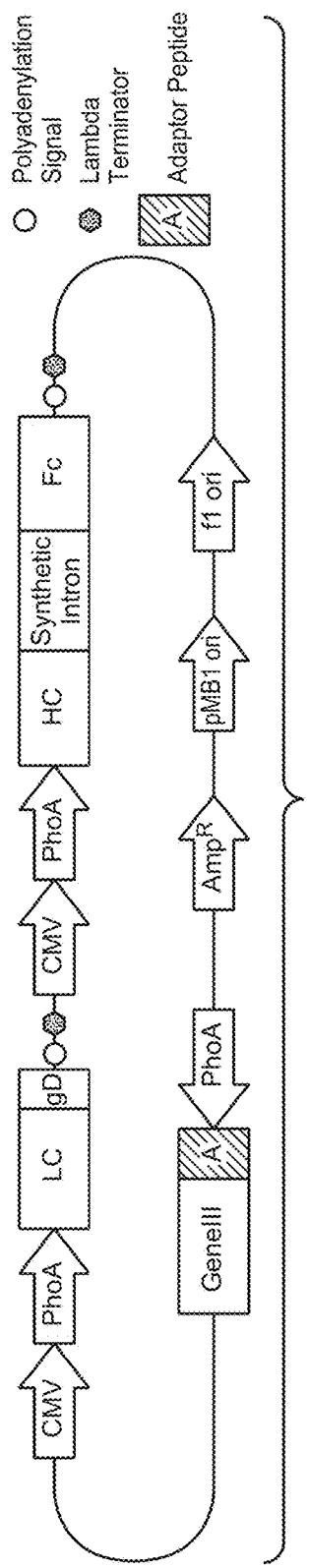

FIG. 12

| Clone | CDR-H1 (30 31 32 33) | CDR-H2 (49 50 51 52 52A 53 54 55 56 57 58) | CDR-H3 (93 94 95 96 97 98 ... 101 102) | CDR-H3 Length |
|---|---|---|---|---|
| VEGF50 | T S Y A | G G I S P Y G G N T Y | A R P G P G G F D S Y Y Y G . . . M D Y | 16 |
| VEGF51 | T D Y A | G G F I Y P Y S G D T Y | A R E V H W Y Y S V . . . . . M D Y | 12 |
| VEGF52 | S S Y G | G G W I Y P N S G N T Y | A R F G Y D V L R Y W D I Y Y G . M A Y | 17 |
| VEGF59 | S N T S | G G W I Y P Y G G S T N | A R F G Y Q R E V Q F S D H Y Y A . M D Y | 18 |
| VEGF55 | S G T Y | G G F I S P Y D G Y T D | A R L Q F N T M W V . . . . . M D Y | 11 |
| VEGF60 | S S Y A | G G S I N P N S G N T Y | A R I G S L C F D C N L Y Y G . M D Y | 18 |
| VEGF61 | S S T A | G G A I T P Y S G N T Y | A R I G S K W S A F D H Y Y A . M D Y | 18 |
| VEGF64 | S S Y A | G G S I N P N S G Y T N | A R T G F G G L V D W S L Y Y G . M D Y | 18 |

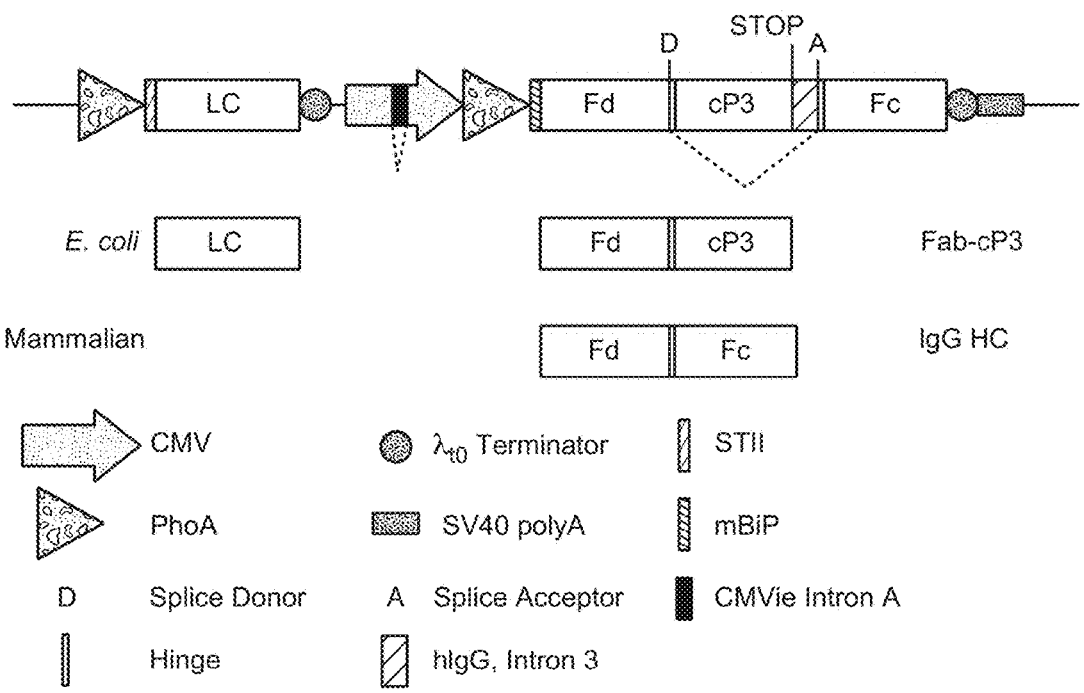

FIG. 14

IgG expression and binding properties clones selected with hVEGF

| Clone Name | Phage ELISA | IgG Expression (mg)[a] | BIAcore (IgG)[b] | BV ELISA Score | VEGF-R1 IC$_{50}$ (nM) |
|---|---|---|---|---|---|
| VEGF50 | + | 0.15 | + | 0.22 | >10 |
| VEGF51 | + | 0.22 | + | 0.28 | >10 |
| VEGF52 | + | 0.21 | + | 0.32 | >10 |
| VEGF55 | + | 0.24 | + | 0.40 | 0.6 |
| VEGF59 | + | 0.06 | + | 0.29 | >10 |
| VEGF60 | + | 0.15 | + | 0.24 | >10 |
| VEGF61 | + | 0.12 | + | 0.23 | >10 |
| VEGF64 | + | 0.20 | + | 0.21 | >10 |

[a] Expression yields from 100 mL CHO cell cultures are indicated.

[b] The BIAcore assay was run using crude supernatant from 1 mL 293T cell cultures whereas the BV ELISA and VEGF-R1 blocking assays were performed using purified material from CHO cultures.

FIG. 15

SEQUENCE LISTING

```
<160> NUMBER OF SEQ ID NOS: 48

<210> SEQ ID NO 1
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ala Glu Asp Ile Glu Phe Ala Ser Gly Gly Gly Ser Gly Ala Glu Thr
1               5                   10                  15

Val Glu Ser Cys Leu Ala Lys Pro His Thr Glu Asn Ser Phe Thr Asn
            20                  25                  30

Val Trp Lys Asp Asp Lys Thr Leu Asp Arg Tyr Ala Asn Tyr Glu Gly
        35                  40                  45

Cys Leu Trp Asn Ala Thr Gly Val Val Val Cys Thr Gly Asp Glu Thr
    50                  55                  60

Gln Cys Tyr Gly Thr Trp Val Pro Ile Gly Leu Ala Ile Pro Glu Asn
65                  70                  75                  80

Glu Gly Gly Gly Ser Glu Gly Gly Gly Ser Glu Gly Gly Gly Ser Glu
                85                  90                  95

Gly Gly Gly Thr Lys Pro Pro Glu Tyr Gly Asp Thr Pro Ile Pro Gly
            100                 105                 110

Tyr Thr Tyr Ile Asn Pro Leu Asp Gly Thr Tyr Pro Pro Gly Thr Glu
        115                 120                 125

Gln Asn Pro Ala Asn Pro Asn Pro Ser Leu Glu Glu Ser Gln Pro Leu
    130                 135                 140

Asn Thr Phe Met Phe Gln Asn Asn Arg Phe Arg Asn Arg Gln Gly Ala
145                 150                 155                 160

Leu Thr Val Tyr Thr Gly Thr Val Thr Gln Gly Thr Asp Pro Val Lys
                165                 170                 175

Thr Tyr Tyr Gln Tyr Thr Pro Val Ser Ser Lys Ala Met Tyr Asp Ala
            180                 185                 190

Tyr Trp Asn Gly Lys Phe Arg Asp Cys Ala Phe His Ser Gly Phe Asn
        195                 200                 205
```

Glu Asp Pro Phe Val Cys Glu Tyr Gln Gly Gln Ser Ser Asp Leu Pro
    210                 215                 220

Gln Pro Pro Val Asn Ala Gly Gly Gly Ser Gly Gly Gly Ser Gly Gly
225                 230                 235                 240

Gly Ser Glu Gly Gly Ser Glu Gly Gly Ser Glu Gly Gly Gly
            245                 250                 255

Ser Glu Gly Gly Gly Ser Gly Gly Ser Gly Ser Gly Asp Phe Asp
        260                 265                 270

Tyr Glu Lys Met Ala Asn Ala Asn Lys Gly Ala Met Thr Glu Asn Ala
            275                 280                 285

Asp Glu Asn Ala Leu Gln Ser Asp Ala Lys Gly Lys Leu Asp Ser Val
    290                 295                 300

Ala Thr Asp Tyr Gly Ala Ala Ile Asp Gly Phe Ile Gly Asp Val Ser
305                 310                 315                 320

Gly Leu Ala Asn Gly Asn Gly Ala Thr Gly Asp Phe Ala Gly Ser Asn
            325                 330                 335

Ser Gln Met Ala Val Gly Asp Gly Asp Asn Ser Pro Leu Met Asn Asn
        340                 345                 350

Phe Arg Gln Tyr Leu Pro Ser Leu Pro Gln Ser Val Glu Cys Arg Pro
    355                 360                 365

Phe Val Phe Ser Ala Gly Lys Pro Tyr Glu Phe Ser Ile Asp Cys Asp
370                 375                 380

Lys Ile Asn Leu Phe Arg Gly Val Phe Ala Phe Leu Leu Tyr Val Ala
385                 390                 395                 400

Thr Phe Met Tyr Val Phe Ser Thr Phe Ala Asn Ile Leu Arg Asn Lys
            405                 410                 415

Glu Ser

<210> SEQ ID NO 2
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Gly Gly Gly Ser Gly Ser Gly Asp Phe Asp Tyr Glu Lys Met Ala
1               5                   10                  15

Asn Ala Asn Lys Gly Ala Met Thr Glu Asn Ala Asp Glu Asn Ala Leu
            20                  25                  30

Gln Ser Asp Ala Lys Gly Lys Leu Asp Ser Val Ala Thr Asp Tyr Gly
        35                  40                  45

Ala Ala Ile Asp Gly Phe Ile Gly Asp Val Ser Gly Leu Ala Asn Gly
    50                  55                  60

Asn Gly Ala Thr Gly Asp Phe Ala Gly Ser Asn Ser Gln Met Ala Gln
65                  70                  75                  80

Val Gly Asp Gly Asp Asn Ser Pro Leu Met Asn Asn Phe Arg Gln Tyr
                85                  90                  95

Leu Pro Ser Leu Pro Gln Ser Val Glu Cys Arg Pro Phe Val Phe Gly
            100                 105                 110

Ala Gly Lys Pro Tyr Glu Phe Ser Ile Asp Cys Asp Lys Ile Asn Leu
        115                 120                 125

Phe Arg Gly Val Phe Ala Phe Leu Leu Tyr Val Ala Thr Phe Met Tyr
    130                 135                 140

```
Val Phe Ser Thr Phe Ala Asn Ile Leu Arg Asn Lys Glu Ser
145                 150                 155
```

```
<210> SEQ ID NO 3
<211> LENGTH: 19
<212> TYPE: PRT
<213> ORGANISM: Mus sp.

<400> SEQUENCE: 3

Met Met Lys Phe Thr Val Val Ala Ala Ala Leu Leu Leu Leu Gly Ala
1               5                   10                  15

Val Arg Ala

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgatgaaat taccgtggt ggcggcggcg ctgctgctgc tgggcgcggt ccgcgcg         57

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (12)..(12)
<223> OTHER INFORMATION: a, c, t or g
<220> FEATURE:
<221> NAME/KEY: modified_base
<222> LOCATION: (15)..(15)
<223> OTHER INFORMATION: a, c, t or g
<220> FEATURE:
<221> NAME/KEY: modified_base
<222> LOCATION: (18)..(18)
<223> OTHER INFORMATION: a, c, t or g
<220> FEATURE:
<221> NAME/KEY: modified_base
<222> LOCATION: (21)..(21)
<223> OTHER INFORMATION: a, c, t or g
<220> FEATURE:
<221> NAME/KEY: modified_base
<222> LOCATION: (24)..(24)
<223> OTHER INFORMATION: a, c, t or g
<220> FEATURE:
<221> NAME/KEY: modified_base
<222> LOCATION: (27)..(27)
<223> OTHER INFORMATION: a, c, t or g
<220> FEATURE:
<221> NAME/KEY: modified_base
<222> LOCATION: (30)..(30)
<223> OTHER INFORMATION: a, c, t or g
<220> FEATURE:
<221> NAME/KEY: modified_base
<222> LOCATION: (33)..(33)
<223> OTHER INFORMATION: a, c, t or g
<220> FEATURE:
<221> NAME/KEY: modified_base
<222> LOCATION: (36)..(36)
<223> OTHER INFORMATION: a, c, t or g
<220> FEATURE:
```

<221> NAME/KEY: modified_base
<222> LOCATION: (39)..(39)
<223> OTHER INFORMATION: a, c, t or g
<220> FEATURE:
<221> NAME/KEY: modified_base
<222> LOCATION: (42)..(42)
<223> OTHER INFORMATION: a, c, t or g
<220> FEATURE:
<221> NAME/KEY: modified_base
<222> LOCATION: (45)..(45)
<223> OTHER INFORMATION: a, c, t or g
<220> FEATURE:
<221> NAME/KEY: modified_base
<222> LOCATION: (48)..(48)
<223> OTHER INFORMATION: a, c, t or g
<220> FEATURE:
<221> NAME/KEY: modified_base
<222> LOCATION: (51)..(51)
<223> OTHER INFORMATION: a, c, t or g
<220> FEATURE:
<221> NAME/KEY: modified_base
<222> LOCATION: (54)..(54)
<223> OTHER INFORMATION: a, c, t or g
<220> FEATURE:
<221> NAME/KEY: modified_base
<222> LOCATION: (57)..(57)
<223> OTHER INFORMATION: a, c, t or g

<400> SEQUENCE: 5
atgatgaant tnacngtngt ngcngcngcn ctnctnctnc tnggngcngt ncgngcn    57

<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Ser Ile Ala Arg Leu Arg Glu Arg Val Lys Thr Leu Arg Ala Arg
1               5                   10                  15

Asn Tyr Glu Leu Arg Ser Arg Ala Asn Met Leu Arg Glu Arg Val Ala
            20                  25                  30

Gln Leu Gly Gly Cys
        35

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Ser Leu Asp Glu Leu Glu Ala Glu Ile Glu Gln Leu Glu Glu Glu
1               5                   10                  15

Asn Tyr Ala Leu Glu Lys Glu Ile Glu Asp Leu Glu Lys Glu Leu Glu
            20                  25                  30

Lys Leu Gly Gly Cys
        35

<210> SEQ ID NO 8
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Glu Glu Lys Ser Arg Leu Leu Glu Lys Glu Asn Arg Glu Leu Glu Lys
1               5                   10                  15

Ile Ile Ala Glu Lys Glu Glu Arg Val Ser Glu Leu Arg His Gln Leu
            20                  25                  30

Gln Ser Val Gly Gly Cys
        35

<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Thr Ser Arg Leu Glu Gly Leu Gln Ser Glu Asn His Arg Leu Arg Met
1               5                   10                  15

Lys Ile Thr Glu Leu Asp Lys Asp Leu Glu Glu Val Thr Met Gln Leu
            20                  25                  30

Gln Asp Val Gly Gly Cys
        35

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: This region may encompass 'Met' or 'Met-Thr' or
      be absent

<400> SEQUENCE: 10

Met Thr Met Lys Phe Thr Val Val Ala Ala Leu Leu Leu Leu Gly
1               5                   10                  15

Ala Val Arg Ala
            20

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: This region may encompass 'ATG' or 'ATGACC' or
      be absent
<220> FEATURE:
<221> NAME/KEY: modified_base
<222> LOCATION: (12)..(12)
<223> OTHER INFORMATION: a, c, t or g
<220> FEATURE:
<221> NAME/KEY: modified_base
<222> LOCATION: (15)..(15)
<223> OTHER INFORMATION: a, c, t or g
<220> FEATURE:
<221> NAME/KEY: modified_base
<222> LOCATION: (18)..(18)

<223> OTHER INFORMATION: a, c, t or g
<220> FEATURE:
<221> NAME/KEY: modified_base
<222> LOCATION: (21)..(21)
<223> OTHER INFORMATION: a, c, t or g
<220> FEATURE:
<221> NAME/KEY: modified_base
<222> LOCATION: (24)..(24)
<223> OTHER INFORMATION: a, c, t or g
<220> FEATURE:
<221> NAME/KEY: modified_base
<222> LOCATION: (27)..(27)
<223> OTHER INFORMATION: a, c, t or g
<220> FEATURE:
<221> NAME/KEY: modified_base
<222> LOCATION: (30)..(30)
<223> OTHER INFORMATION: a, c, t or g
<220> FEATURE:
<221> NAME/KEY: modified_base
<222> LOCATION: (33)..(33)
<223> OTHER INFORMATION: a, c, t or g
<220> FEATURE:
<221> NAME/KEY: modified_base
<222> LOCATION: (36)..(36)
<223> OTHER INFORMATION: a, c, t or g
<220> FEATURE:
<221> NAME/KEY: modified_base
<222> LOCATION: (39)..(39)
<223> OTHER INFORMATION: a, c, t or g
<220> FEATURE:
<221> NAME/KEY: modified_base
<222> LOCATION: (42)..(42)
<223> OTHER INFORMATION: a, c, t or g
<220> FEATURE:
<221> NAME/KEY: modified_base
<222> LOCATION: (45)..(45)
<223> OTHER INFORMATION: a, c, t or g
<220> FEATURE:
<221> NAME/KEY: modified_base
<222> LOCATION: (48)..(48)
<223> OTHER INFORMATION: a, c, t or g
<220> FEATURE:
<221> NAME/KEY: modified_base
<222> LOCATION: (51)..(51)
<223> OTHER INFORMATION: a, c, t or g
<220> FEATURE:
<221> NAME/KEY: modified_base
<222> LOCATION: (54)..(54)
<223> OTHER INFORMATION: a, c, t or g
<220> FEATURE:
<221> NAME/KEY: modified_base
<222> LOCATION: (57)..(57)
<223> OTHER INFORMATION: a, c, t or g
<220> FEATURE:
<221> NAME/KEY: modified_base
<222> LOCATION: (60)..(60)
<223> OTHER INFORMATION: a, c, t or g

<400> SEQUENCE: 11
atgaccatga anttnacngt ngtngcngcn gcnctnctnc tnctnggngc ngtncgngcn    60

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Ser Ile Ala Arg Leu Glu Glu Lys Val Lys Thr Leu Lys Ala Gln
1               5                   10                  15

Asn Tyr Glu Leu Ala Ser Thr Ala Asn Met Leu Arg Glu Gln Val Ala
            20                  25                  30

Gln Leu Gly Gly Cys
        35

<210> SEQ ID NO 13
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Ser Ile Asp Glu Leu Gln Ala Glu Val Glu Gln Leu Glu Glu Arg
1               5                   10                  15

Asn Tyr Ala Leu Arg Lys Glu Val Glu Asp Leu Gln Lys Gln Ala Glu
            20                  25                  30

Lys Leu Gly Gly Cys
        35

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Gly Ser Cys
1

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Pro Pro Cys Pro Gly
1               5

<210> SEQ ID NO 16
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atgatgaaat taccgttgt tgctgctgct ctgctacttc ttggagcggt ccgcgca        57

<210> SEQ ID NO 17
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
atgatgaaat tactgttgt tgcggctgct cttctccttc ttggagcggt ccgcgca        57

<210> SEQ ID NO 18

<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 18
atgatgaaat ttactgttgt cgctgctgct cttctacttc ttggagcggt ccgcgca   57

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 19

Met Thr Met Lys Phe Thr Val Val Ala Ala Ala Leu Leu Leu Leu Gly
1               5                   10                  15

Ala Val Arg Ala
            20

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 20

Met Lys Phe Thr Val Val Ala Ala Ala Leu Leu Leu Leu Gly Ala Val
1               5                   10                  15

Arg Ala

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (12)..(12)
<223> OTHER INFORMATION: a, c, t or g
<220> FEATURE:
<221> NAME/KEY: modified_base
<222> LOCATION: (15)..(15)
<223> OTHER INFORMATION: a, c, t or g
<220> FEATURE:
<221> NAME/KEY: modified_base
<222> LOCATION: (18)..(18)
<223> OTHER INFORMATION: a, c, t or g
<220> FEATURE:
<221> NAME/KEY: modified_base
<222> LOCATION: (21)..(21)
<223> OTHER INFORMATION: a, c, t or g
<220> FEATURE:
<221> NAME/KEY: modified_base
<222> LOCATION: (24)..(24)
<223> OTHER INFORMATION: a, c, t or g
<220> FEATURE:
<221> NAME/KEY: modified_base
<222> LOCATION: (27)..(27)
<223> OTHER INFORMATION: a, c, t or g
<220> FEATURE:
<221> NAME/KEY: modified_base
<222> LOCATION: (30)..(30)

-continued

```
<223> OTHER INFORMATION: a, c, t or g
<220> FEATURE:
<221> NAME/KEY: modified_base
<222> LOCATION: (33)..(33)
<223> OTHER INFORMATION: a, c, t or g
<220> FEATURE:
<221> NAME/KEY: modified_base
<222> LOCATION: (36)..(36)
<223> OTHER INFORMATION: a, c, t or g
<220> FEATURE:
<221> NAME/KEY: modified_base
<222> LOCATION: (39)..(39)
<223> OTHER INFORMATION: a, c, t or g
<220> FEATURE:
<221> NAME/KEY: modified_base
<222> LOCATION: (42)..(42)
<223> OTHER INFORMATION: a, c, t or g
<220> FEATURE:
<221> NAME/KEY: modified_base
<222> LOCATION: (45)..(45)
<223> OTHER INFORMATION: a, c, t or g
<220> FEATURE:
<221> NAME/KEY: modified_base
<222> LOCATION: (48)..(48)
<223> OTHER INFORMATION: a, c, t or g
<220> FEATURE:
<221> NAME/KEY: modified_base
<222> LOCATION: (51)..(51)
<223> OTHER INFORMATION: a, c, t or g
<220> FEATURE:
<221> NAME/KEY: modified_base
<222> LOCATION: (54)..(54)
<223> OTHER INFORMATION: a, c, t or g
<220> FEATURE:
<221> NAME/KEY: modified_base
<222> LOCATION: (57)..(57)
<223> OTHER INFORMATION: a, c, t or g
<220> FEATURE:
<221> NAME/KEY: modified_base
<222> LOCATION: (60)..(60)
<223> OTHER INFORMATION: a, c, t or g

<400> SEQUENCE: 21
atgaccatga anttnacngt ngtngcngcn gcnctnctnc tnctnggngc ngtncgngcn     60

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: a, c, t or g
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (12)..(12)
<223> OTHER INFORMATION: a, c, t or g
<220> FEATURE:
<221> NAME/KEY: modified_base
<222> LOCATION: (15)..(15)
<223> OTHER INFORMATION: a, c, t or g
<220> FEATURE:
<221> NAME/KEY: modified_base
<222> LOCATION: (18)..(18)
<223> OTHER INFORMATION: a, c, t or g
<220> FEATURE:
<221> NAME/KEY: modified_base
<222> LOCATION: (21)..(21)
<223> OTHER INFORMATION: a, c, t or g
<220> FEATURE:
```

```
<221> NAME/KEY: modified_base
<222> LOCATION: (24)..(24)
<223> OTHER INFORMATION: a, c, t or g
<220> FEATURE:
<221> NAME/KEY: modified_base
<222> LOCATION: (27)..(27)
<223> OTHER INFORMATION: a, c, t or g
<220> FEATURE:
<221> NAME/KEY: modified_base
<222> LOCATION: (30)..(30)
<223> OTHER INFORMATION: a, c, t or g
<220> FEATURE:
<221> NAME/KEY: modified_base
<222> LOCATION: (33)..(33)
<223> OTHER INFORMATION: a, c, t or g
<220> FEATURE:
<221> NAME/KEY: modified_base
<222> LOCATION: (36)..(36)
<223> OTHER INFORMATION: a, c, t or g
<220> FEATURE:
<221> NAME/KEY: modified_base
<222> LOCATION: (39)..(39)
<223> OTHER INFORMATION: a, c, t or g
<220> FEATURE:
<221> NAME/KEY: modified_base
<222> LOCATION: (42)..(42)
<223> OTHER INFORMATION: a, c, t or g
<220> FEATURE:
<221> NAME/KEY: modified_base
<222> LOCATION: (45)..(45)
<223> OTHER INFORMATION: a, c, t or g
<220> FEATURE:
<221> NAME/KEY: modified_base
<222> LOCATION: (48)..(48)
<223> OTHER INFORMATION: a, c, t or g
<220> FEATURE:
<221> NAME/KEY: modified_base
<222> LOCATION: (51)..(51)
<223> OTHER INFORMATION: a, c, t or g
<220> FEATURE:
<221> NAME/KEY: modified_base
<222> LOCATION: (54)..(54)
<223> OTHER INFORMATION: a, c, t or g

<400> SEQUENCE: 22
atgaanttna cngtngtngc ngcngcnctn ctnctnctng gngcngtncg ngcn         54

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtgaattatc accgtcaccg acctaggcca tttgggaatt agagcca              47

<210> SEQ ID NO 24
<211> LENGTH: 1275
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gtgaaaaaat tattattcgc agttcctttta gttgttcctt tctattctca ctcagctgag    60
actgttgaaa gttgtttagc aaaaccccat acagaaaatt catttactaa cgtctggaaa   120
gacgacaaaa ctttagatcg ttacgctaac tatgagggtt gtctgtggaa tgctacaggc   180
gttgtagttt gtactggtga cgaaactcag tgttacggta catgggttcc tattgggctt   240
```

```
gctatccctg aaaatgaggg tggtggctct gagggtggcg ttctgaggg tggcggttct      300 gagggtggcg gtactaaacc tcctgagtac ggtgatacac ctattccggg ctatacttat      360
atcaaccctc tcgacggcac ttatccgcct ggtactgagc aaaacccgc taatcctaat      420 ccttctcttg aggagtctca gcctcttaat actttcatgt tcagaataa taggttccga      480 aataggcagg gggcattaac tgtttatacg ggcactgtta ctcaaggcac tgacccgtt      540 aaaacttatt accagtacac tcctgtatca tcaaaagcca tgtatgacgc ttactggaac      600
ggtaaattca gagactgcgc tttccattct ggctttaatg aggatccatt cgtttgtgaa      660
tatcaaggcc aatcgtctga cctgcctcaa cctcctgtca atgctggcgg cggctctggt      720
ggtggttctg gtggcggctc tgagggtggt ggctctgagg gtggcggttc tgagggtggc      780
ggctctgagg gaggcggttc cggtggtggc tctggttccg gtgattttga ttatgaaaag      840
atggcaaacg ctaataaggg ggctatgacc gaaaatgccg atgaaaacgc gctacagtct      900
gacgctaaag gcaaacttga ttctgtcgct actgattacg gtgctgctat cgatggtttc      960
attggtgacg tttccggcct tgctaatggt aatggtgcta ctggtgattt gctggctct     1020 aattcccaaa tggcctaggt cggtgacggt gataattcac ctttaatgaa taatttccgt     1080
caatatttac cttccctccc tcaatcggtt gaatgtcgcc cttttgtctt tagcgctggt     1140
aaaccatatg aattttctat tgattgtgac aaaataaact tattccgtgg tgtctttgcg     1200
tttcttttat atgttgccac ctttatgtat gtatttccta cgtttgctaa catactgcgt     1260
aataaggagt cttaa                                                      1275
```

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Ser Tyr Ala
1

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Ile Ser Pro Tyr Gly Gly Asn Thr Tyr
1               5                   10

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Pro Gly Pro Gly Gly Gly Phe Asp Ser Tyr Tyr Tyr Gly Met
1               5                   10                  15

Asp Tyr

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Asp Tyr Ala
1

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Phe Ile Tyr Pro Tyr Ser Gly Asp Thr Tyr
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Arg Glu Val His Phe Trp Tyr Tyr Ser Val Met Asp Tyr
1               5                   10

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ser Tyr Gly
1

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Trp Ile Tyr Pro Asn Ser Gly Asn Thr Tyr
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic -continued

```
<400> SEQUENCE: 33

Ala Arg Phe Gly Tyr Asp Val Leu Arg Tyr Trp Asp Tyr Tyr Tyr Gly
1               5                   10                  15

Met Ala Tyr

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Asn Thr Ser
1

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Trp Ile Tyr Pro Tyr Gly Gly Ser Thr Asn
1               5                   10

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Arg Phe Gly Tyr Gln His Glu Val Gln Phe Ser Asp His Tyr Tyr
1               5                   10                  15

Ala Met Asp Tyr
            20

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Gly Thr Tyr
1

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

```
Gly Phe Ile Ser Pro Tyr Asp Gly Tyr Thr Asp
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Arg Leu Gln Phe Asn Thr Met Trp Val Met Asp Tyr
1               5                   10

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Ser Tyr Ala
1

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ser Ile Asn Pro Asn Ser Gly Tyr Thr Asn
1               5                   10

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Arg Ile Gly Phe Gly Ser Leu Cys Phe Asp Cys Asn Leu Tyr Tyr
1               5                   10                  15

Gly Met Asp Tyr
            20

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ser Thr Ala
1

<210> SEQ ID NO 44
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Gly Ile Thr Pro Tyr Ser Gly Asn Thr Tyr
1               5                   10

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Arg Ile Gly Ser Gly Ser His Trp Ser Ala Phe Asp His Tyr Tyr
1               5                   10                  15

Ala Met Asp Tyr
            20

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Ser Tyr Ala
1

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Ser Ile Asn Pro Asn Ser Gly Tyr Thr Asn
1               5                   10

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Arg Thr Gly Phe Gly Gly Ile Val Val Asp Trp Ser Leu Tyr Tyr
1               5                   10                  15

Gly Met Asp Tyr
            20
```

EXPRESSION AND SECRETION SYSTEM

CROSS REFERENCE TO RELATED APPLICATIONS

This application claims benefit from U.S. Provisional Application Nos. 61/668,397 filed on 5 Jul. 2012, 61/852,483 filed on 15 Mar. 2013, and 61/819,063 filed on 3 May 2013, all of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jul. 2, 2013, is named P4825R1-US_SL.txt and is 24,691 bytes in size.

FIELD OF THE INVENTION

The present invention relates to an expression and secretion system, and methods for its use, for the expression and secretion of one Fab fusion protein when the nucleic acid is transformed into a prokaryotic cell for phage display and a distinct or identical Fab fusion protein when the nucleic acid is transfected into an eukaryotic cell for expression and purification. Also provided herein are nucleic acid molecules, vectors and host cells comprising such vectors and nucleic acid molecules.

BACKGROUND

Phage display of peptides or proteins on filamentous phage particles is an in vitro technology which allows the selection of peptides or proteins with desired properties from large pools of variant peptides or proteins (McCafferty et al., Nature, 348: 552-554 (1990); Sidhu et al., Current Opinion in Biotechnology, 11: 610-616 (2000); Smith et al., Science, 228: 1315-1317 (1985)). Phage display may be used to display diverse libraries of peptides or proteins, including antibody fragments, such as Fabs in the antibody discovery field, on the surface of a filamentous phage particle which are then selected for binding to a particular antigen of interest. The antibody fragment may be displayed on the surface of the filamentous phage particle by fusing the gene for the antibody fragment to that of a phage coat protein, resulting in a phage particle that displays the encoded antibody fragment on its surface. This technology allows the isolation of antibody fragments with desired affinity to many antigens form a large phage library.

For phage-based antibody discovery, evaluation of selected antibody fragments and the properties of their cognate IgGs in functional assays (such as target binding, cell-based activity assays, in vivo half-life, etc.) requires reformatting of the Fab heavy chain (HC) and light chain (LC) sequences into a full-length IgG by subcloning the DNA sequences encoding the HC and LC out of the vector used for phage display and into mammalian expression vectors for IgG expression. The laborious process of sub-cloning dozens or hundreds of selected HC/LC pairs represents a major bottleneck in the phage-based antibody discovery process. Furthermore, since a substantial percentage of selected Fabs, once reformatted, fail to perform satisfactorily in initial screening assays, increasing the number of clones carried through this reformatting/screening process greatly increases the ultimate probability of success.

Here, we describe the generation of an expression and secretion system for driving expression of a Fab-phage fusion when transformed into E. coli, and of driving expression of a full-length IgG bearing the same Fab fragment when transfected into mammalian cells. We demonstrate that a mammalian signal sequence from the murine binding immunoglobulin protein (mBiP) (Haas et al., Immunoglobulin heavy chain binding protein, Nature, 306: 387-389 (1983); Munro et al., An Hsp70-like protein in the ER: identify with the 78 kd glucose-regulated protein and immunoglobulin heavy chain binding protein, Cell, 4:291-300 (1986) can drive efficient protein expression in both prokaryotic and eukaryotic cells. Using mammalian mRNA splicing to remove a synthetic intron containing a phage fusion peptide inserted within the hinge region of the human $IgG_1$ HC, we are able to generate two distinct proteins in a host cell-dependent fashion: a Fab fragment fused to an adaptor peptide for phage display in E. coli and native human $IgG_1$ in mammalian cells. This technology allows for the selection of Fab fragments that bind to an antigen of interest from a phage display library with subsequent expression and purification of the cognate full-length IgGs in mammalian cells without the need for subcloning.

SUMMARY

In one aspect, the invention is based, in part, on experimental findings demonstrating that (1) signal sequences of non-prokaryotic origin function in prokaryotic cells and (2) different Fab-fusion proteins are expressed from the same nucleic acid molecule in a host-cell dependent manner when mRNA processing occurs in eukaryotic cells, but not prokaryotic cells (Fab-phage fusion proteins in prokaryotic cells and Fab-Fc fusion proteins in eukaryotic cells). Accordingly, described herein are nucleic acid molecules for the expression and secretion of a Fab fragment fused to a phage particle protein, coat protein or adaptor protein for phage display in bacteria when the nucleic acid is transformed into prokaryotic host cells (e.g. E. coli) and a Fab fragment fused to Fc when the nucleic acid is transformed into eukaryotic cells (e.g. mammalian cells), without the need for subcloning, and methods of use.

In one embodiment, the invention provides a nucleic acid molecule encoding a first polypeptide comprising VH-HVR1, VH-HVR2 and HVR3 of a variable heavy chain domain (VH) and/or a second polypeptide comprising VL-HVR1, VL-HVR2 and VL-HVR3 of a variable light chain domain, and wherein the nucleic acid molecule further encodes a signal sequence which is functional in both a prokaryotic and an eukaryotic cell and is encoded by a nucleic acid sequence that is operably linked to the first and/or second polypeptide sequence, and wherein a full-length antibody is expressed from the first and/or second polypeptide of the nucleic acid molecule. In another embodiment, the first and/or second polypeptide further comprises a variable heavy chain (VH) domain and a variable light chain (VL) domain. In a further embodiment, the VH domain is linked to CH1 and the VL domain is linked to CL.

In one aspect, the present invention provides a nucleic acid molecule, encoding VH-HVR1, VH-HVR2 and VH-HVR3 of a variable heavy chain domain (VH) and VL-HVR1, VL-HVR2 and VL-HVR3 of a variable light chain domain (VL) and comprising a prokaryotic promoter and an eukaryotic promoter which promoters are operably linked to the HVRs of the VH and/or the HVRS of the VL to allow for expression of the HVRs of the VH and the HVRs of the VL in a prokaryotic and a eukaryotic cell, and wherein the HVRs of the VH and/or VL is linked to a utility peptide when expressed by a eukaryotic cell and wherein the nucleic acid further encodes a signal sequence which is functional in both a prokaryotic and an eukaryotic cell.

In another aspect, the present invention provides a nucleic acid molecule encoding a variable heavy chain (VH) domain and a variable light chain (VL) domain and comprising a prokaryotic promoter and an eukaryotic promoter which promoters are operably linked to the VH domain and/or VL domain to allow for expression of a VH domain and/or a VL domain in a prokaryotic and a eukaryotic cell, and wherein the VH domain and/or VL is linked to a utility peptide when expressed by a eukaryotic cell and wherein the nucleic acid further encodes a signal sequence which functions in both a prokaryotic and an eukaryotic cell.

In one embodiment, the VL and VH are linked to utility peptides. In a further embodiment, the VH is further linked to a CH1 and the VL is linked to a CL. The utility peptide is selected from the group consisting of a Fc, tag, label and control protein. In one embodiment the VL is linked to a control protein and the VH is linked to a Fc. For example, the control protein is a gD protein, or a fragment thereof.

In an even further embodiment the first and/or second polypeptide of the invention is fused to a coat protein (e.g. pI, pII, pIII, pIV, pV, pVI, pVII, pVIII, pIX and pX of bacteriophage M13, f1 or fd, or a fragment thereof such as amino acids 267-421 or 262-418 of the pIII protein ("pI", "pII", "pIII", "pIV", "pV", "pVI", "pVII", "pVIII", "pIX", and "pX" when used herein refers to the full-length protein or fragments thereof unless specified otherwise)) or an adaptor protein (e.g. a leucine zipper protein or a polypeptide comprising an amino acid sequence of SEQ ID NO: 12 (cJUN(R): ASIARLEEKV KTLKAQNYEL ASTANMLRE Q VAQLGGC) or SEQ ID NO: 13 (FosW(E): ASIDELQAE V EQLEERNYAL RKEVEDLQKQ AEKLGGC) or a variant thereof (amino acids in SEQ ID NO: 12 and SEQ ID NO: 13 that may be modified include, but are not limited to those that are underlined and in bold), wherein the variant has an amino acid modification wherein the modification maintains or increases the affinity of the adaptor protein to another adaptor protein, or a polypeptide comprising the amino acid sequence selected from the group consisting of SEQ ID NO: 6 (ASIARLRERVKTLRARNYELRSRANMLR-ERVAQLGGC) or SEQ ID NO: 7 (ASLDELE-AEIEQLEEENYALEKEIEDLEKELEKLGGC)) or a polypeptide comprising an amino acid sequence of SEQ ID NO: 8 (GABA-R1: EEKSRLLEKE NRELEKIIAE KEERVSELRH QLQSVGGC) or SEQ ID NO: 9 (GABA-R2: TSRLEGLQSE NHRLRMKITE LDKDLEEVTM QLQDVGGC) or SEQ ID NO: 14 (Cys: AGSC) or SEQ ID NO: 15 (Hinge: CPPCPG). The nucleic acid molecule encoding for the coat protein or adaptor protein is comprised within a synthetic intron. The synthetic intron is located between the nucleic acid encoding for the VH domain and the nucleic acid encoding for the Fc. The synthetic intron further comprises nucleic acid encoding for a naturally occurring intron from IgG1 wherein the naturally occurring intron may selected from the group comprising intron 1, intron 2 or intron 3 from IgG1.

In one embodiment, the invention provides a nucleic acid molecule, wherein in prokaryotic cells, a first fusion protein is expressed and in eukaryotic cells, a second fusion protein is expressed. The first fusion protein and the second fusion protein may be the same or different. In a further embodiment, the first fusion protein may be a Fab-phage fusion protein (e.g the Fab-phage fusion protein comprises VH/CH1 fused to the pIII) and the second fusion may be a Fab-Fc or Fab-hinge-Fc fusion protein (e.g. the Fab-Fc or Fab-hinge-Fc fusion protein comprises VH/CH1 fused to Fc).

In one embodiment, the invention provides a nucleic acid molecule, wherein the signal sequence directs protein secretion to the endoplasmic reticulum or outside of the cell in eukaryotic cells and/or wherein the signal sequence directs protein secretion to the periplasm or outside of the cell in prokaryotic cells. Further, the signal sequence may be encoded by a nucleic acid sequence which encodes for the amino acid sequence comprising the amino acid sequence of SEQ ID NO: 10 (XMKFTVVAAALLLLGAVRA, wherein X=0 amino acids or 1 or 2 amino acids (e.g. X=M (SEQ ID NO: 3; MMKFTVVAAALLLLGAVRA; wild-type mBIP) or X=MT (SEQ ID NO: 19; MTMKFTVVAAALLLL-GAVRA) or X is absent (SEQ ID NO: 20; MKFTV-VAAALLLLGAVRA) or by a nucleic acid sequence which encodes mBIP (SEQ ID NO: 4; ATG ATG AAA TTT ACC GTG GTG GCG GCG GCG CTG CTG CTG CTG GGC GCG GTC CGC GCG), and variants thereof, or by a nucleic acid sequence which encodes for an amino acid sequence having at least 90% amino acid sequence identity to an amino acid sequence selected from SEQ ID NO: 3 (mBIP amino acid sequence), and wherein the signal sequence functions in both prokaryotic and eukaryotic cells, or by the nucleic acid sequence of SEQ ID NO: 11 (consensus mBIP sequence, X ATG AAN TTN ACN GTN GTN GCN GCN GCN CTN CTN CTN CTN GGN GCN GTN CGN GCN, wherein N=A, T, C or G, wherein X=ATG (SEQ ID NO: 5; ATG ATG AAN TTN ACN GTN GTN GCN GCN GCN CTN CTN CTN CTN GGN GCN GTN CGN GCN), X=ATG ACC (SEQ ID NO: 21; ATG ACC ATG AAN TTN ACN GTN GTN GCN GCN GCN CTN CTN CTN CTN GGN GCN GTN CGN GCN) or X=is absent (SEQ ID NO: 22; ATG AAN TTN ACN GTN GTN GCN GCN GCN CTN CTN CTN CTN GGN GCN GTN CGN GCN). or by a nucleic acid sequence selected from the group of SEQ ID NO: 16 (mBIP.Opt1: ATG ATG AAA TTT ACC GTT GTT GCT GCT GCT CTG CTA CTT CTT GGA GCG GTC CGC GCA), SEQ ID NO: 17 (mBIP.Opt2: ATG ATG AAA TTT ACT GTT GTT GCG GCT GCT CTT CTC CTT CTT GGA GCG GTC CGC GCA) and SEQ ID NO: 18 (mBIP.Opt3: ATG ATG AAA TTT ACT GTT GTC GCT GCT GCT CTT CTA CTT CTT GGA GCG GTC CGC GCA).

In a further embodiment, the synthetic intron in the nucleic acid molecule is flanked by nucleic acid encoding the CH1 at its 5' end and nucleic acid encoding the Fc at its 3' end. Further, the nucleic acid encoding the CH1 domain comprises a portion of the natural splice donor sequence and the nucleic acid encoding the Fc comprises a portion of the natural splice acceptor sequence. Alternatively, the nucleic acid encoding the CH1 domain comprises a portion of a modified splice donor sequence wherein the modified splice donor sequence comprises modification of at least one nucleic acid residue and wherein the modification increases splicing.

In one embodiment, the prokaryotic promoter is phoA, Tac, Tphac or Lac promoter and/or the eukaryotic promoter is CMV or SV40 or Moloney murine leukemia virus U3 region or caprine arthritis-encephalitis virus U3 region or visna virus U3 region or retroviral U3 region sequence. Expression by the prokaryotic promoter occurs in a bacteria cell and expression by a eukaryotic promoter occurs in a mammalian cell. In a further embodiment, the bacteria cell is an *E. coli* cell and the eukaryotic cell is a yeast cell, CHO cell, 293 cell or NSO cell.

In another embodiment, the present invention provides a vector comprising the nucleic acid molecules described herein and/or a host cell transformed with such vectors. The host cell may be a bacterial cell (e.g. an *E. coli* cell) or an eukaryotic cell (e.g. yeast cell, CHO cell, 293 cell or NSO cell).

In another embodiment, the present invention provides a process for producing an antibody comprising culturing the host cell described herein such that the nucleic acid is expressed. The process further comprises recovering the antibody expressed by the host cell and wherein the antibody is recovered from the host cell culture medium.

In one aspect, the invention provides an adaptor protein comprising a modification of at least one residue of the amino acid sequence of SEQ ID NO: 8, 9, 12, 13, 14 or 15. In one embodiment, the amino acid sequence is selected from the group consisting of SEQ ID NO: 6 (ASIARLR-ERVKTLRARNYELRSRANMLRERVAQLGGC) or SEQ ID NO: 7 (ASLDELEAEIEQLEEENYALEKEIEDLE-KELEKLGGC). In one embodiment, the invention provides for nucleic acids encoding such adaptor proteins.

In one aspect, the invention provides a nucleic acid molecule encoding a mBIP polypeptide comprising the amino acid sequence of SEQ ID NO: 3 or variants thereof, which is functional in both prokaryotic and eukaryotic cells, or a polypeptide having an amino acid sequence with 85% homology with the amino acid sequence of SEQ ID NO: 3. In one embodiment, the invention provides a method of expressing a mBIP polypeptide comprising the amino acid sequence of SEQ ID NO: 3 or variants thereof in both prokyarotic and eukaryotic cells. In one embodiment, the invention provides a bacterial cell that expresses a mBIP sequence comprising the amino acid sequence of SEQ ID NO: 3, or variants thereof.

In one aspect, the invention provides that the synthetic intron is located between the nucleic acid encoding for the VH domain and the nucleic acid encoding for the Fc or the hinge of the antibody, between the CH2 and the CH3 domain of the antibody, between the nucleic acid encoding for the hinge region and the CH2 domain of the antibody.

In one aspect, the invention comprises a polypeptide comprising a signal sequence comprising the amino acid sequence of SEQ ID NO: 3, or variants thereof, a variable heavy chain domain (VH) and a variable light chain domain (VL) wherein the VH domain is connected to the N-terminus of the VL domain, or a polypeptide comprising a signal sequence comprising the amino acid sequence of SEQ ID NO: 3, or variants thereof, a variable heavy chain domain (VH) and a variable light chain domain (VL) wherein the VH domain is connected to the C-terminus of the VL domain, or a polypeptide comprising a signal sequence comprising the amino acid sequence of SEQ ID NO: 3 and a VH-HVR1, VH-HVR2, and VH-HVR3 of a variable heavy chain domain (VH), or a polypeptide comprising a signal sequence comprising the amino acid sequence of SEQ ID NO: 3 and a VL-HVR1, VL-HVR2, and VL-HVR3 of a variable light chain domain (VL), or a polypeptide comprising a signal sequence comprising the amino acid sequence of SEQ ID NO: 3, or variants thereof, a VH-HVR1, VH-HVR2, and VH-HVR3 of a variable heavy chain domain (VH) and a VL-HVR1, VL-HVR2 and VL-HVR3 of a variable light chain domain (VL). In one embodiment, the polypeptide of the invention is an antibody or antibody fragment. The antibody or antibody fragment of the invention may be selected from the group consisting of F(ab')2 and Fv fragments, diabodies, and single-chain antibody molecules.

In one aspect, the invention comprises a mutant helper phage for enhancing phage display of proteins. In one embodiment, the nucleotide sequence of a helper phage comprising an amber mutation in pIII wherein the helper phage comprising an amber mutation enhances display of proteins fused to pIII on phage. In a further embodiment, the amber mutation is a mutation in nucleotides 2613, 2614 and 2616 of the nucleic acid for M13KO7. In an even further embodiment, the mutation in nucleotides 2613, 2614 and 2616 of the nucleic acid for M13KO7 introduces an amber stop codon.

BRIEF DESCRIPTION OF THE FIGURES

FIG. 5. (A) Point mutations generated in the natural Intron1 splice donor to increases conformity to the consensus splice donor for mammalian mRNAs. (B) Optimization of the intron splice donor eliminates the accumulation of unspliced and incorrectly spliced HC mRNA and (C) increases expression in mammalian cells to the level observed when no intron is present FIG. 6. (A) Modulation of display using pDV.5.0 and either wild-type KO7 (monovalent display) or adaptor KO7 (polyvalent display). (B) Expression of four different mAbs from pDV.5.0 in three different mammalian cell lines.

FIG. 7. Schematic of vector for expression and secretion of polypeptides in prokaryotic and eukaryotic cells. The synthetic intron may contain either an adaptor sequence, or a phage coat protein sequence along with any of the naturally-occurring introns sequences from hIgG1. Both the HC and LC may have either: 1) mammalian AND bacterial promoters upstream of the ORF, 2) a bacterial promoter ONLY upstream of the ORF (see also FIG. 14), or 3) a mammalian promoter only upstream of the ORF. A construct in which both HC and LC have both promoter types is shown. The cassette containing gene-III with an adaptor peptide fusion (pDV5.0, shown) is only present when the synthetic intron contains an adaptor peptide fusion, but not when a phage coat protein fusion is present in the synthetic intron.

FIG. 8. Nucleotide sequence of the pIII (nucleotides 1579 to 2853 (SEQ ID NO: 24)) of mutant helper phage Amber KO7 to enhance display of proteins fused to pIII on M13 phage. Amber KO7 has an amber codon introduced in the M13KO7 helper phage genome by site directed mutagenesis. The underlined residues are mutations in nucleotides 2613, 2614 and 2616 (T2613C, C2614T and A2616G) that introduce an amber stop (TAG) in codon 346 and a silent mutation for an AvrII restriction site in codon 345 of M13KO7 gene III. Nucleotide 1 of M13KO7 is the third residue of the unique HpaI restriction site.

FIG. 12 shows the sequences of positive binders from the VEGF panning experiment in Example 5. The heavy chain CDR sequence for eight clones (VEGF50 (SEQ ID NOS 25-27, respectively, in order of appearance), VEGF51 (SEQ ID NOS 28-30, respectively, in order of appearance), VEGF 52 (SEQ ID NOS 31-33, respectively, in order of appearance), VEGF59 (SEQ ID NOS 34-36, respectively, in order of appearance), VEGF55 (SEQ ID NOS 37-39, respectively, in order of appearance), VEGF60 (SEQ ID NOS 40-42, respectively, in order of appearance), VEGF61 (SEQ ID NOS 43-45, respectively, in order of appearance) and VEGF64 (SEQ ID NOS 46-48, respectively, in order of appearance)) is shown. All clones share the same light chain CDR sequence.

FIG. 14 shows a schematic of vector for expression and secretion of polypeptides in prokaryotic and eukaryotic cells, wherein the synthetic intron contains pIII, along with any of the naturally-occurring introns sequences from hIgG1 and wherein the LC has a bacterial promoter upstream of the ORF and the HC has both a mammalian and bacterial promoter upstream of the ORF. Unlike the vector shown in FIG. 7, this vector (pDV6.5) does not require an additional gIII cassette for fusion to phage particles. The proteins resulting from expression in *E. coli* and mammalian cells are shown below the vector schematic. The dashed lines indicate introns in the heavy chain transcript spliced in mammalian cells. Note that part of the sequence encoding the IgG1 hinge is repeated in the vector to allow inclusion in both *E. coli* and mammalian cell expressed proteins.

FIG. 15 shows properties of full-length anti-VEGF IgGs expressed from pDV6.5. IgGs were expressed in 100 mL transfected CHO cell cultures and purified by protein A chromatography. Final yields of purified IgG are indicated along with the score in a baculovirus ELISA used to measure non-specific binding. The positive or negative binding of each clone in phage format (phage ELISA) or IgG format (BIAcore) is also indicated.

DETAILED DESCRIPTION OF EMBODIMENTS OF THE INVENTION

I. DEFINITIONS

Figure 1A:
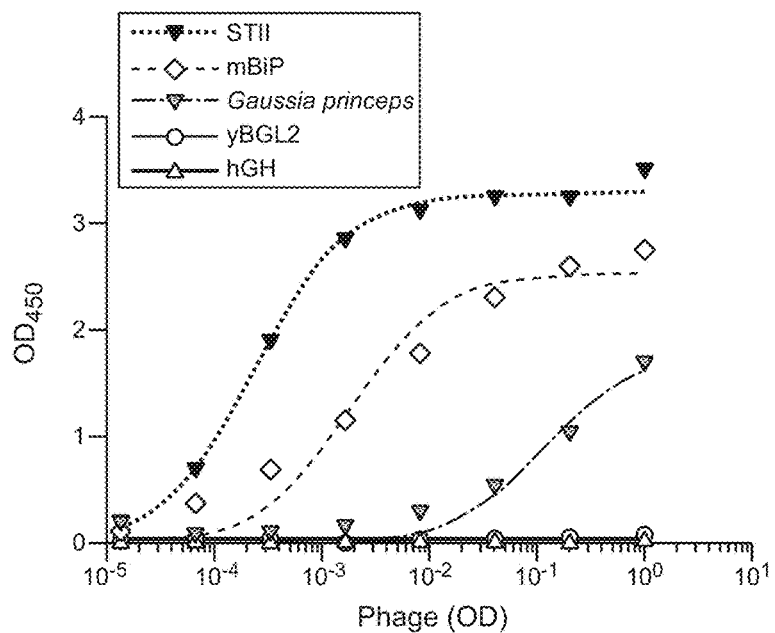
FIG. 1. (A) Her2 phage ELISA of purified phage displaying anti-Her2 Fab under the control of four different eukaryotic signal sequences (mBiP, Gaussia princeps, yBGL2, hGH). The heat-stable enterotoxin II (STII) prokaryotic signal sequence commonly used in phagemids serves as a benchmark. (B) Phage display of anti-Her2 Fab fused to wild-type eukaryotic mBiP signal sequence (mBiP.wt) and the codon optimized versions obtained by phage library panning (mBiP.Opt1, mBiP.Opt2 and mBip.Opt3 (SEQ ID NOs: 16-18)).

The term "synthetic intron" herein is used to define a segment of nucleic acid that is situated between the nucleic acid encoding the CH1 and the nucleic acid encoding the Hinge-Fc or Fc. The "synthetic intron" may be any nucleic acid which does not encode for protein synthesis, any nucleic acid which does encode for protein synthesis, such as a phage particle protein or coat protein (e.g pI, pII, pIII, pIV, pV, pVI, pVII, pVIII, pIX, pX), or an adaptor protein (e.g. a leucine-zipper, etc.), or any combination thereof. In one embodiment, the "synthetic intron" comprises part of a splice donor sequence and a splice acceptor sequence which allow a splice event. The splice donor and splice acceptor sequences allow the splice event and may comprise natural or synthetic nucleic acid sequences.

The term "utility polypeptide" herein is used to refer to a polypeptide that is useful for a number of activities, such as useful for protein purification, protein tagging, protein labeling (e.g. labeling with a detectable compound or composition (e.g. radioactive label, fluorescent label or enzymatic label). A label may be indirectly conjugated with an amino acid side chain, an activated amino acid side chain, a cysteine engineered antibody, and the like. For example, the antibody can be conjugated with biotin and any of the three broad categories of labels mentioned above can be conjugated with avidin or streptavidin, or vice versa. Biotin binds selectively to streptavidin and thus, the label can be conjugated with the antibody in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in Bioconjugate Techniques Academic Press, San Diego).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the linked DNA sequences exist in a nucleic acid molecule in such a way that they have a functional relationship with each other as nucleic acids or as proteins that are expressed by them. They may be contiguous or not. In the case of a secretory leader, they are often contiguous and in reading phase. However, enhancers do not have to be contiguous. Linking is accomplished by ligation at convenient restriction sites. If such sites do not exist, the synthetic oligonucleotide adaptors or linkers can be used.

VH or VL domains are "linked" to a phage when the nucleic acid encoding the heterologous protein sequence (for example, VH or VL domains) is inserted directly into the nucleic acid encoding a phage coat protein (for example, pII, pVI, pVII, pVIII or pIX). When introduced into a prokaryotic cell, a phage will be produced in which the coat protein can display the VH or VL domains. In one embodiment, the resulting phage particles display antibody fragments fused to the amino or carboxy termini of phage coat proteins.

The terms "linked" or "links" or "link" as used herein are meant to refer to the covalent joining of two amino acids sequences or two nucleic acid sequences together through peptide or phosphodiester bonds, respectively, such joining can include any number of additional amino acid or nucleic acid sequences between the two amino acid sequences or nucleic acid sequences that are being joined. For example, there can be a direct peptide bond linkage between a first and second amino acid sequence or a linkage that involves one or more amino acid sequences between the first and second amino acid sequences.

By "linker" as used herein is meant an amino acid sequence of two or more amino acids in length. The linker can consist of neutral polar or nonpolar amino acids. A linker can be, for example, 2 to 100 amino acids in length, such as between 2 and 50 amino acids in length, for example, 3, 5, 10, 15, 20, 25, 30, 35, 40, 45, or 50 amino acids in length. A linker can be "cleavable," for example, by auto-cleavage, or enzymatic or chemical cleavage. Cleavage sites in amino acid sequences and enzymes and chemicals that cleave at such sites are well known in the art and are also described herein.

The term "signal sequence functions" refers to the biological activity of a signal sequence directing secreted proteins to the ER (in eukaryotes) or periplasm (in prokaryotes) or outside of the cell.

A "control protein" as used herein refers to a protein sequence whose expression is measured to quantitate the level of display of the protein sequence. For example, the protein sequence can be an "epitope tag" that enables the VH or VL to be readily purified by affinity purification using an anti-tag antibody or another type of affinity matrix that binds to the epitope tag. Examples of tag polypeptides and their respective antibodies that are suitable include: poly-histidine (poly-His) or poly-histidine-glycine (poly-His-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

A "coat protein" as used herein refers to any of the five capsid proteins that are components of phage particles, including pIII, pVI, pVII, pVIII and pIX. In one embodiment, the "coat protein" may be used to display proteins or peptides (see Phage Display, A Practical Approach, Oxford University Press, edited by Clackson and Lowman, 2004, p. 1-26). In one embodiment, a coat protein may be the pIII protein or some variant, part and/or derivative thereof. For example, a C-terminal part of the M13 bacteriophage pIII coat protein (cP3), such as a sequence encoding the C-terminal residues 267-421 of protein III of M13 phage may be used. In one embodiment, the pIII sequence comprises the amino acid sequence of SEQ ID NO: 1 (AEDIEFASGGGSGAETVESCLAKPHTENSFTNVWK-DDKTLDRYANYEGCLWNATGV VVCTGDETQCYG-TWVPIGLAIPENEGGGSEGGGSEGGGSEGGGTKPP-EYGDTPIPGYT YINPLDGTYPPGTEQNPANPNPSL-EESQPLNTFMFQNNRFRNRQGALTVYTGTVTQGT DPVKTYYQYTPVSSKAMYDAYWNGKFRDCAFHS-GFNEDPFVCEYQGQSSDLPQPPV NAGGGSGGG-SGGGSEGGGSEGGGSEGGGSEGGGSGGGSGSGD-FDYEKMANANKGA MTENADENALQSDAKGKLDS-VATDYGAAIDGFIGDVSGLANGNGATGDFAGSNSQM AVGDGDNSPLMNNFRQYLPSLPQSVECRPFVFSAGK-PYEFSIDCDKINLFRGVFAFLLY VATFMYVFSTFANIL-RNKES). In one embodiment, the pIII fragment comprises the amino acid sequence of SEQ ID NO: 2 (SGGGSGSGDFDYEKMANANKGAMTENADE-NALQSDAKGKLDSVATDYGAAIDGFI GDVSGLANGNGATGDFAGSNSQ-MAQVGDGDNSPLMNNFRQYLPSLPQSVECRPFVFG AGKPYEFSIDCDKINLFRGVFAFLLYVATFMYVFST-FANILRNKES).

An "adaptor protein" as used herein refers to a protein sequence that specifically interacts with another adaptor protein sequence in solution. In one embodiment, the "adaptor protein" comprises a heteromultimerization domain. In one embodiment, the adaptor protein is a cJUN protein or a Fos protein. In another embodiment, the adaptor protein comprises the sequence of SEQ ID NO: 6 (ASIARLR-ERVKTLRARNYELRSRANMLRERVAQLGGC) or SEQ ID NO: 7 (ASLDELEAEIEQLEEENYALEKEIEDLE-KELEKLGGC).

As used herein, "heteromultimerization domain" refers to alterations or additions to a biological molecule so as to promote heteromultimer formation and hinder homomultimer formation. Any heterodimerization domain having a strong preference for forming heterodimers over homodimers is within the scope of the invention. Illustrative examples include but are not limited to, for example, US Patent Application 20030078385 (Arathoon et al.—Genentech; describing knob into holes); WO2007147901 (Kjægaard et al.—Novo Nordisk: describing ionic interactions); WO 2009089004 (Kannan et al.—Amgen: describing electrostatic steering effects); WO2011/034605 (Christensen et al.—Genentech; describing coiled coils). See also, for example, Pack, P. & Plueckthun, A., Biochemistry 31, 1579-1584 (1992) describing leucine zipper or Pack et al., Bio/Technology 11, 1271-1277 (1993) describing the helix-turn-helix motif. The phrase "heteromultimerization domain" and "heterodimerization domain" are used interchangeably herein.

The term "Fab-fusion protein" is used herein to refer to a Fab-phage fusion protein in prokaryotic cells and/or a Fab-Fc fusion protein in eukaryotic cells. The Fab-Fc fusion may also be a Fab-hinge-Fc fusion.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVR5). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. DETAILED DESCRIPTION

The phage-based antibody discovery process utilizes phage display technology to select Fab fragments with desired binding specificities from large pools of individual phage clones[1-3]. In this approach, phage libraries comprised of Fab fragments fused to M13 filamentous phage particles, either directly or indirectly through one of the major coat proteins and containing diversified complementarity determining regions (CDRs), are generated using established molecular biology techniques and specialized phage display vectors (Tohidkia et al., *Journal of drug targeting*, 20: 195-208 (2012); Bradbury et al., *Nature biotechnology*, 29: 245-254 (2011); Qi et al., *Journal of molecular biology*, 417: 129-143 (2012)). While the theoretical diversity of such libraries can easily exceed $10^{25}$ unique sequences, practical limitations in the construction of phage pools typically constrains the actual diversity to $\leq 10^{11}$ clones for a given library (Sidhu et al., *Methods in enzymology*, 328: 333-363 (2000)).

Given the substantial number of unique sequences that a starting library may contain, the screening throughput of selected clones is of critical importance. For phage-based antibody discovery, a thorough evaluation of selected Fabs and the properties of their cognate full-length IgGs in functional assays (target binding, cell-based activity assays, in vivo half-life, etc.) requires reformatting of the Fab heavy chain (HC) and light chain (LC) sequences into a full-length IgG by subcloning the DNA sequences encoding the HC and LC out of the phagemid vector used for display and into mammalian expression vectors for IgG expression. The laborious process of subcloning dozens or hundreds of selected HC/LC pairs represents a major bottleneck in the phage-based antibody discovery process. Furthermore, since a substantial percentage of selected Fabs, once reformatted, fail to perform satisfactorily in initial screening assays, increasing the number of clones carried through this reformatting/screening process greatly increases the ultimate probability of success.

Here, we describe the generation of an expression and secretion system for the expression and secretion of one Fab fusion protein in prokaryotic cells and a distinct (or identical) Fab fusion in eukaryotic cells. For example, the expression and secretion system drives expression of a Fab-phage fusion when transformed into *E. coli*, and drives expression of a full-length IgG bearing the same Fab fragment when transfected into mammalian cells. We demonstrate that a mammalian signal sequence from the murine binding immunoglobulin protein (mBiP)[8,9] can drive efficient protein expression in both prokaryotic and eukaryotic cells. Using mammalian mRNA splicing to remove a synthetic intron containing a phage fusion peptide inserted within the hinge region of the human $IgG_1$ HC, we are able to generate two distinct proteins in a host cell-dependent fashion: a Fab fragment fused to an adaptor peptide for phage display in *E. coli* and native human $IgG_1$ in mammalian cells. This technology allows for the selection of Fab fragments that bind to an antigen of interest from a phage display library with subsequent expression and purification of the cognate full-length IgGs in mammalian cells without the need for subcloning.

The invention is based, in part, on experimental findings demonstrating that (1) signal sequences of non-bacterial origin function in prokaryotic cells at levels sufficient for sorting of phage libraries without compromising IgG expression in eukaryotic cells, and (2) different Fab-fusion proteins are expressed from the same nucleic acid molecule in a host-cell dependent manner when mRNA processing occurs in eukaryotic cells, but not prokaryotic cells (Fab-phage fusion proteins in prokaryotic cells and Fab-Fc fusion proteins in eukaryotic cells). Accordingly, described herein is an expression and secretion system for the expression and secretion of a Fab fragment fused to a phage particle protein, coat protein or adaptor protein for phage display in prokaryotic host cells (e.g. E. coli) and a Fab fragment fused to Fc in eukaryotic cells (e.g. mammalian cells), without the need for subcloning, and methods relating to the construction and use of the expression and secretion system. In particular, vectors for expression and secretion of a Fab-phage fusion protein in prokaryotic cells and a Fab-Fc fusion protein in eukaryotic cells, nucleic acid molecules for expression and secretion or proteins or peptides in prokaryotic and eukaryotic cells, and host cells comprising such vectors are described herein. Further, methods of use of the expression and secretion system, including methods of use of the expression and secretion system for screening and selection of novel antibodies against proteins of interest, is described herein.

MODES OF CARRYING OUT THE INVENTION

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Expression and Secretion System for Prokaryotic and Eukaryotic Cells

The expression and secretion system for prokaryotic and eukaryotic cells involves a vector which contains the regulatory and coding sequences for a protein of interest (e.g. the heavy or light chains of an IgG molecule), wherein prokaryotic and eukaryotic promoters (e.g. CMV (eukaryotic) and PhoA (prokaryotic)) are arranged in tandem upstream of the gene(s) of interest, and a single signal sequences drives the expression of the protein of interest in prokaryotic and eukaryotic cells. The present invention provides a means for this vector to generate two different fusion forms of the protein of interest in a host-cell dependent manner by using a synthetic intron located between the VH/CH1 and the hinge-Fc region of IgG1 wherein the synthetic intron is spliced out during mRNA processing in eukaryotic cells.

A. Signal Sequence that Functions in Both Prokaryotic and Eukaryotic Cells

One challenge in constructing a vector capable of expressing proteins of interest in both prokaryotic (E. coli) and eukaryotic (mammalian) cells arises from differences in signal sequences found in these cell types. While certain features of signal sequences are generally conserved in both prokaryotic and eukaryotic cells (e.g. a patch of hydrophobic residues located in the middle of the sequence and polar/charged residues adjacent to the cleavage site at the N-terminus of the mature polypeptide), others are more characteristic of one cell type than the other. Moreover, it is known in the art that different signal sequences can have significant impact on expression levels in mammalian cells, even if the sequences are all of mammalian origin (Hall et al., *J of Biological Chemistry*, 265: 19996-19999 (1990); Humphreys et al., *Protein Expression and Purification*, 20: 252-264 (2000)). For instance, bacterial signal sequences typically have positively-charged residues (most commonly lysine) directly following the initiating methionine, whereas these are not always present in mammalian signal sequences. While there are known signal sequences capable of directing secretion in both cell types, such signal sequences typically direct high levels of protein secretion in only one cell type or the other.

While bacterial signal sequences have very rarely been shown to exhibit any functionality in mammalian cells, there have been reports of signal sequences of mammalian origin being capable of driving translocation into the periplasm of bacteria (Humphreys et al., *The Protein Expression and Purification*, 20: 252-264 (2000)). However, mere functionality of the signal sequence is not adequate for a robust dual expression system to be used for phage display and IgG expression. Rather, the selected signal sequence must function well in both expression systems, particularly for phage display where low levels of display would compromise the ability of the system to perform phage panning experiments.

The present invention is based in part on the discovery that signal sequences of non-bacterial origin function in prokaryotic cells at levels sufficient for sorting of phage libraries without compromising IgG expression in eukaryotic cells.

The present invention provides any signal sequence (including concensus signal sequences) which targets the polypeptide of interest to the periplasm in prokaryotes and to the endoplasmic/reticulum in eukaryotes, may be used. Signal sequences that may be used include but are not limited to the murine binding immunoglobulin protein (mBiP) signal sequence (UniProtKB: accession P20029), signal sequences from human growth hormone (hGH) (UniProtKB: accession BIA4G6), Gaussia princeps luciferase (UniProtKB: accession Q9BLZ2), yeast endo-1,3-glucanase (yBGL2) (UniProtKB: accession P15703). In one embodiment, the signal sequence is a natural or synthetic signal sequence. In a further embodiment, the synthetic signal sequence is an optimized signal secretion sequence that drives levels of display at an optimized level compared to its non-optimized natural signal sequence.

A suitable assay for determining the ability of signal sequences to drive display of polypeptides of interest in prokaryotic cells, includes, for example, phage ELISA, as described herein.

A suitable assay for determining the ability of signal sequences to drive expression of polypeptides of interest in eukaryotic cells, includes, for example, transfection of mammalian expression vectors encoding the polypeptides of interest with the signal of interest into cultured mammalian cells, growing the cells for a period of time, collecting the supernatants from the cultured cells, and purifying IgG from the supernatants by affinity chromatography, as described herein.

B. Synthetic Intron that Results in Expression of Host-Dependent Fusion Proteins from the Same Nucleic Acid The present invention is based in part on the discovery that different Fab-fusion proteins may be expressed from the same nucleic acid molecule in a host cell dependent manner by exploiting the natural process of intron splicing which occurs during mRNA processing in eukaryotic, but not prokaryotic cells.

The genomic sequence of hIgG1 HC constant region contains three natural introns (FIG. 3A), Intron 1, Intron 2 and Intron 3. Intron 1 is a 391 base pair intron positioned between the HC variable domain/CH1 (VH/CH1) and the hinge region. Intron 2 is a 118 base pair intron positioned between the hinge region and CH2. Intron 3 is a 97 base pair intron positioned between CH2 and CH3.

The present invention provides a vector which comprises Intron 1 positioned between the VH/CH1 and hinge region. Other examples, include Intron 2 or Intron 3 positioned between the VH/CH1 and hinge region. For some vectors, nucleic acid encoding for a coat protein ro an adaptor protein are inserted into the intron positioned between VH/CH1 and the hinge region with the natural plice donor for the intron at its 5' end and the natural splice acceptor at its 3' end. Other examples, include a mutant splice donor with substitutions at positions 1 and 5 out of 8 positions of the splice donor.

For example, phage ELISA may be used to analyze the expression and secretion system in prokaryotic cells.

For example, purification of IgG from culture supernatants using protein A and gel filtration chromatography may be used to analyze the expression and secretion system in eukaryotic cells. Further, RT-PCR may be used to analyze the splicing of the synthetic intron-containing HC cassette in eukaryotic cells.

C. Vector for Expression and Secretion of Polypeptides in Prokaryotic and Eukaryotic Cells The expression and secretion system for expression and secretion of Fab-fusion proteins in prokaryotic and eukaryotic cells may be constructed using a variety of techniques which are within the skill of the art.

In one aspect, the expression and secretion system comprises a vector comprising: (1) a mammalian promoter, (2) LC cassette, comprising (in order from 5' to 3') a bacterial promoter, a signal sequence, an antibody light chain sequence, a control protein (gD); (3) synthetic cassette comprising (in order from 5' to 3') a mammalian polyadenylation/transcriptional stop signal, a transcriptional terminator sequence for halting transcription in prokaryotic cells, a mammalian promoter and a bacterial promoter for driving expression of the HC; (4) HC cassette, comprising a signal sequence and an antibody heavy chain sequence; and (5) second synthetic cassette comprising a mammalian polyadenylation/transcriptional stop signal and a transcriptional terminator sequence for halting transcription in prokaryotic cells. The secretional signal sequence preceding the LC and HC may be the same signal sequence that functions in both prokaryotic and eukaryotic cells (e.g. the mammalian mBiP signal sequence). In one embodiment, the antibody heavy chain sequence comprises a synthetic intron. The synthetic intron is positioned with the VH/CH1 domain (at its 5' end) and the hinge region (at its 3' end). In one embodiment, the synthetic intron is flanked by an optimized splice donor sequence at the 5' end and the natural intron 1 splice acceptor sequence at the 3' end. In one embodiment, the synthetic intron comprises a nucleotide sequence which encodes for a phage coat protein (e.g. pIII) for direct fusion display (see FIG. 14), or an adaptor protein fused at the nucleotide level to intron 1 for indirect fusion display (see FIG. 7). For indirect fusion display, the vector further comprises a separate bacterial expression cassette comprising (in order from 5' to 3') bacterial promoter, a bacterial signal sequence, a phage coat protein (e.g. pIII) with a partner adaptor peptide fused at the nucleotide level to the N-terminus of the coat protein and a transcriptional terminator sequence (see FIG. 7). In addition, different embodiments of the above constructs are possible in which both the HC and LC are controlled by a mammalian and bacterial promoter in tandem (see FIG. 7) or only one (e.g., HC) cassette is controlled by tandem mammalian and bacterial promoters whereas the other (e.g., LC) cassette is controlled only by a bacterial promoter (see FIG. 14).

Further, the vector includes a bacterial origin of replication, a mammalian origin of replication, nucleic acid which encodes for polypeptides useful as a control (e.g. gD protein) or useful for activities such as a protein purification, protein tagging, protein labeling (e.g. labeling with a detectable compound or composition (e.g. radioactive label, fluorescent lable or enzymatic label).

In one embodiment, the mammalian and bacterial promoters and signal sequences are operably linked to the antibody light chain sequence and mammalian and bacterial promoters and signal sequences are operably linked to the antibody heavy chain sequence.

D. Selection and Screening of Antibodies Against Antigens of Interest

The present invention provides a method of screening and selecting antibodies against proteins of interest by phage or bacterial display of Fab-based libraries or to optimize existing antibodies by similar methods. Use of the dual vector described above may be used for screening and selecting of Fab fragments in prokaryotic cells, and the selection of Fabs that can be readily expressed as full-length IgG molecules for further testing without the need for subcloning.

Antibodies of Invention

In a further aspect of the invention, an antibody according to any of the above embodiments is a monoclonal antibody, including a chimeric, humanized or human antibody. In one embodiment, an antibody is an antibody fragment, e.g., a Fv, Fab, Fab', scFv, diabody, or F(ab')$_2$ fragment. In another embodiment, the antibody is a full length antibody, e.g., an intact IgG1, IgG2, IgG3 or IgG4 antibody or other antibody class or isotype as defined herein.

In a further aspect, an antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v)

bovine serum albumin in PBS for two to five hours at room temperature (approximately 23° C.). In a non-adsorbent plate (Nunc #269620), 100 μM or 26 μM [$^{125}$I]-antigen antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for a first antigen and the other is for any other antigen. In certain embodiments, bispecific antibodies may bind to two different epitopes of the first antigen. Bispecific antibodies may also be used to localize cytotoxic agents to cells which express the first antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to a first antigen as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). Clq binding assays may also be carried out to confirm that the antibody is unable to bind Clq and hence lacks CDC activity. See, e.g., Clq and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103: 2738-2743 (2004)). FcRn binding and in vivo clearance/half life determinations can also be performed using methods known in the art (see, e.g., Petkova, S. B. et al., *Intl. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Assays

Antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with an antibody of the invention for binding to an antigen of interest. In certain embodiments, such a competing antibody binds to the same epitope (e.g., a linear or a conformational epitope) that is bound by an antibody of the invention. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized antigen of interest is incubated in a solution comprising a first labeled antibody that binds to antigen of interest (e.g., an antibody of the invention) and a second unlabeled antibody that is being tested for its ability to compete with the first antibody for binding to antigen of interest. The second antibody may be present in a hybridoma supernatant. As a control, immobilized antigen of interest is incubated in a solution comprising the first labeled antibody but not the second unlabeled antibody. After incubation under conditions permissive for binding of the first antibody to antigen of interest, excess unbound antibody is removed, and the amount of label associated with immobilized antigen of interest is measured. If the amount of label associated with immobilized antigen of interest is substantially reduced in the test sample relative to the control sample, then that indicates that the second antibody is competing with the first antibody for binding to antigen of interest. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying antibodies thereof having biological activity. Antibodies having such biological activity in vivo and/or in vitro are also provided.

In certain embodiments, an antibody of the invention is tested for such biological activity.

The following examples are offered for illustrative purposes only, and are not intended to limit the scope of the present invention in any way.

All patent and literature references cited in the present specification are hereby expressly incorporated by reference in their entirety.

III. EXAMPLES

The following are examples of methods and compositions of the invention. It is understood that various other embodiments may be practiced, given the general description provided above.

M13KO7 helper phage were from New England Biolabs. Bovine serum albumin (BSA) and Tween 20 were from Sigma. Casein was from Pierce. anti-M13 conjugated horseradish peroxidase (HRP) was from Amersham Pharmacia. Maxisorp immunoplates were from NUNC. Tetramethylbenzidine (TMB) substrate was from Kirkegaard and Perry Laboratories. All other protein antigens were generated by research groups at Genentech, Inc.

Example 1

Selection of Signal Sequence for Expression in Prokaryotic and Eukaryotic Cells

To address whether a vector is capable of expressing proteins of interest in both *Escherichia coli* and eukaryotic (mammalian) cells, four signal sequences of non-bacterial origin for which there was anecdotal evidence supporting the idea that they could function in mammalian cells were selected. We tested these signal sequences for their ability to drive display of an anti-Her2 (h4D5) Fab on M13 phage using a phage ELISA (FIG. 1A). The levels of display were evaluated relative to the bacterial heat-stable enterotoxin II (STII) signal sequence. The capacity of the signal sequences to drive Fab-phage display varied greatly, and one signal sequence, from the murine binding immunoglobulin protein (mBiP), drove levels of display that could possibly allow efficient levels of Fab display.

Figure 1B:
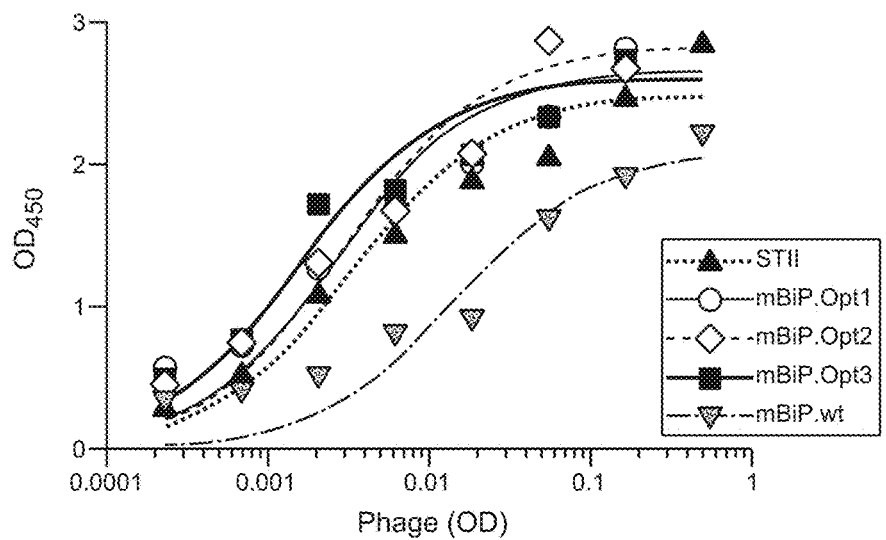

To improve the performance of the mBiP signal sequence further, we utilized a phage-based codon optimization approach, as it has been demonstrated previously that the function of eukaryotic signal sequences in bacteria is greatly affected by codon usage (Humphreys et al., *The Protein Expression and Purification*, 20: 252-264 (2000). A phage library was constructed in which the mBiP signal sequence was fused to the N-terminus of the h4D5 Fab HC in a standard phagemid vector. The DNA sequence of the mBiP signal peptide was diversified in the third base of each codon following the first two methionines allowing only silent mutations. After four rounds of solid-phase panning against immobilized Her2, individual clones were picked and sequenced. We found that the consensus sequence of the selected clones strongly favored an adenine or thymine in the randomized positions rather than a guanine or cytosine. This result is punctuated by the fact that 15 of the 17 codons in the wild-type mBiP sequence contain a guanine or cytosine in the third base position, but each of the 17 codons in the sorted library contained adenine or thymine in these positions 60-90% of the time. When tested in a phage ELISA, the optimized mBiP signal sequence drives display of h4D5 Fab at levels comparable to the prokaryotic STII signal sequence, suggesting that the mBiP signal sequence can be utilized for phage display and panning experiments in place of the prokaryotic STII signal sequence without any apparent reduction in performance (FIG. 1B).

Figure 2A:
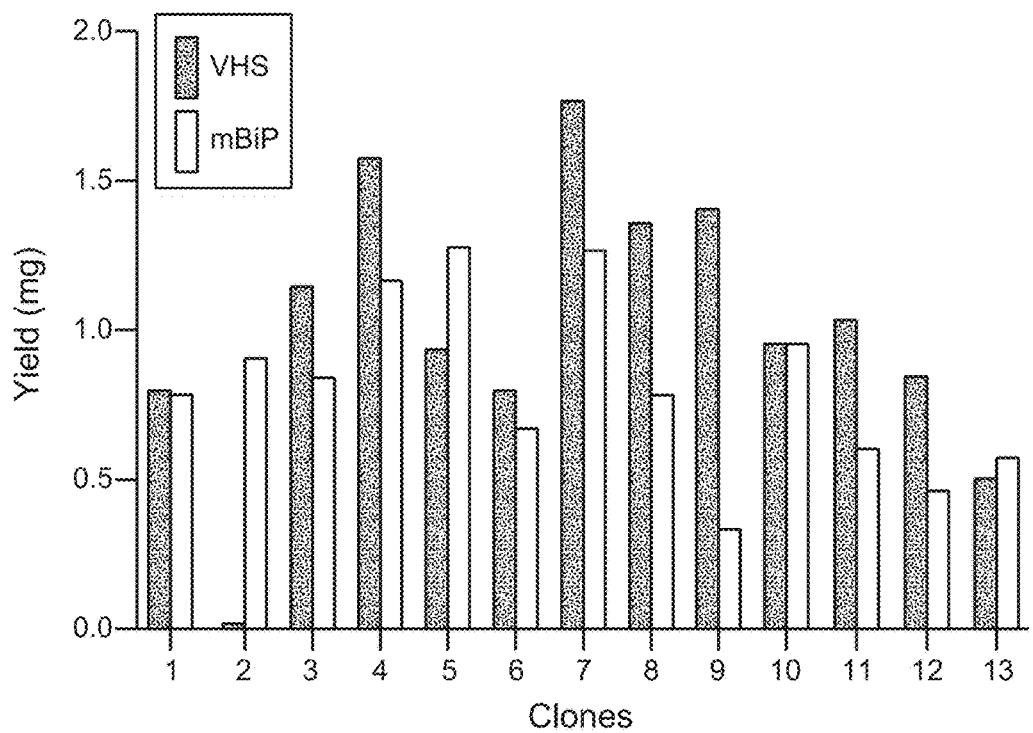
FIG. 2. (A) Expression yields from 30 mL 293 cell suspension cultures of individual clones and (B) aggregate statistics for hIgG1 clones expressed as fusions to either the eukaryotic mBiP or the prokaryotic native IgG HC (VHS) signal sequence.
Figure 2B:
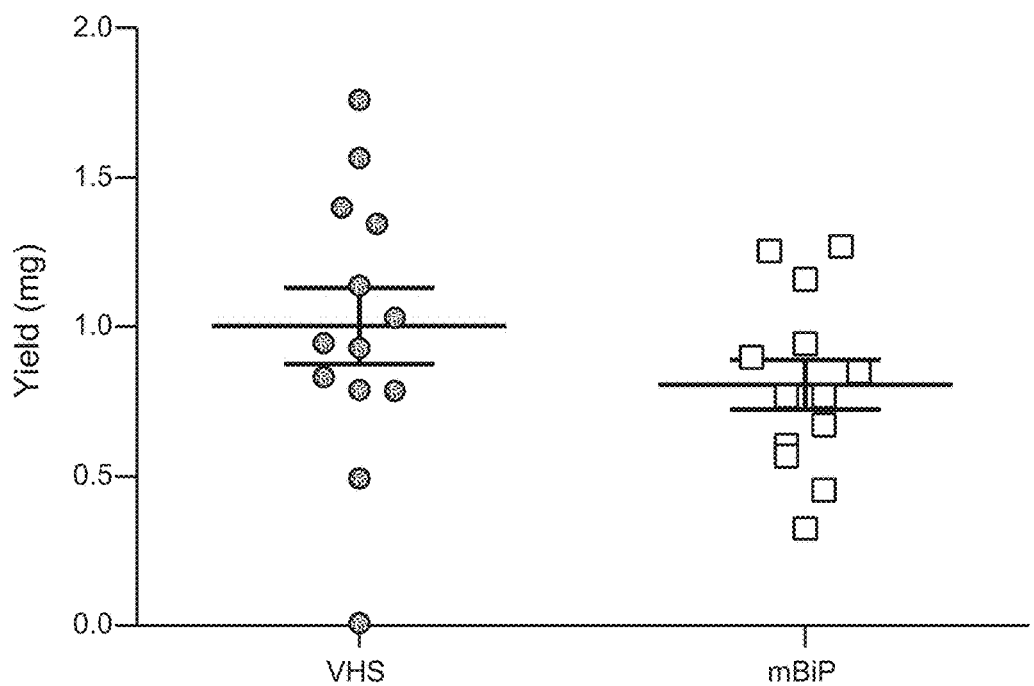

Next, the ability of the mBiP signal sequence to support expression and secretion of IgG in mammalian cells was evaluated. Mammalian expression vectors encoding the HC and LC of h4D5 hIgG$_1$, each with the mBiP signal sequence fused to the N-terminus, were cotransfected into suspension 2935 cells and grown for five days, after which the supernatants were collected and IgG was purified by affinity chromatography. The IgG yield from one 30 mL culture was routinely ~2.0 mg, comparable to the yields obtained using a native HC signal (VHS) in both chains (data not shown). Interestingly, use of the wild-type versus the codon optimized form of the mBiP signal sequence had no discernable effect on IgG expression levels (data not shown). Gel filtration chromatography and mass spectrometry confirmed that the purified protein was >90% monomeric in solution and that the mBiP signal sequence was fully cleaved at the proper position on both HC and LC (data not shown). Because h4D5 is known to be a good expresser, we tested the performance of mBiP relative to VHS on a pool of uncharacterized clones arbitrarily selected from a phage panning experiment. The mean yield from these clones was ~1.0 mg from a 30 mL suspension culture, and no significant differences were observed between the two signal sequences (FIGS. 2A and B).

In summary, the mBiP mammalian secretion signal sequence was capable of expressing IgG in mammalian cells at levels sufficient for screening, and once codon optimized, was also capable of driving robust Fab display on phage without compromising IgG expression levels.

Example 2

Expression of Alternate Fab Fusions in Prokaryotic and Eukaryotic Cells

Figure 3A:
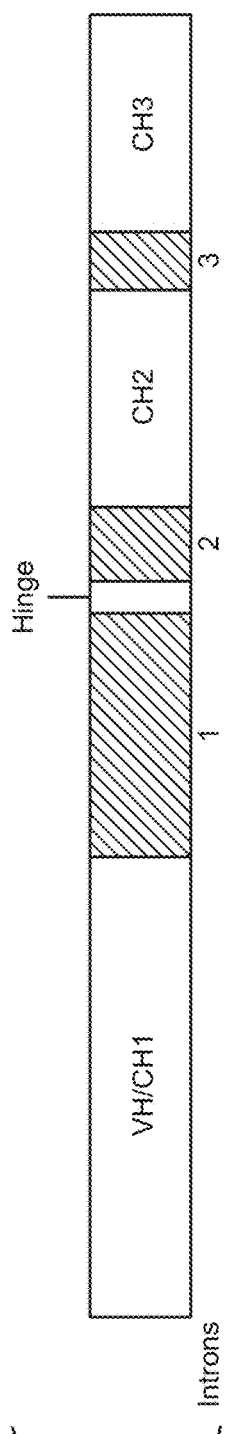
FIG. 3. (A) Genomic structure of human IgG1 HC containing three natural introns. Intron1 occurs immediately prior to the hinge region. (B) HC construct containing a synthetic intron derived from Intron1 or 3 and containing a phage adaptor fusion peptide. The synthetic intron is flanked by the natural intron splice donor (D) and acceptor (A) from Intron1 or 3. (C) HC construct containing a synthetic intron derived from Intron1 or 3 and containing a phage coat fusion protein. The synthetic intron is flanked by the natural intron splice donor (D) and acceptor (A) from Intron1 or 3. Both Construct (B) and (C) contain a STOP codon at the 3' end of the adaptor peptide or phage coat protein sequence.

In order to generate different Fab-fusion proteins in a host cell-dependent manner, we sought to exploit the natural process of intron splicing which occurs during mRNA processing in eukaryotic, but not prokaryotic cells. The genomic sequence of hIgG$_1$ HC constant region contains three natural introns (FIG. 3A). The first of these (Intron1) is a 384 base pair intron positioned between the HC variable domain (V$_H$) and the hinge region. A HC expression vector containing Intron1 and an optimized splice donor sequence expressed fully spliced mRNA as assessed by RT-PCR and sequencing of the transcripts and, when cotransfected with a LC vector, expressed IgG$_1$ at levels comparable to a vector without the intron (FIG. 5).

Figure 3B:
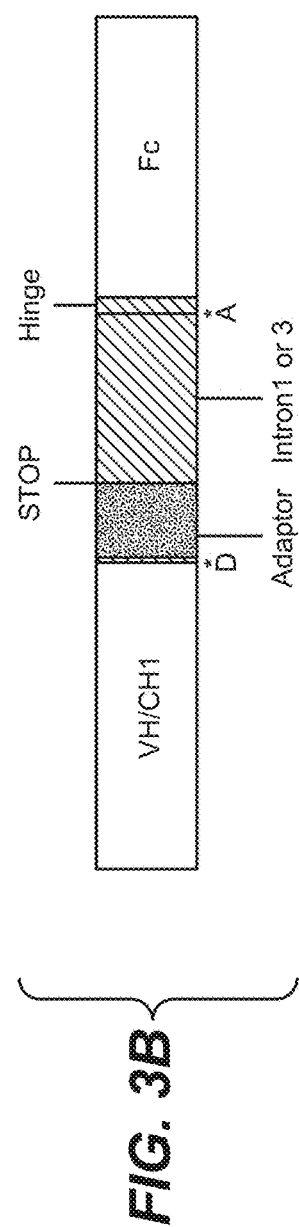
Figure 3C:
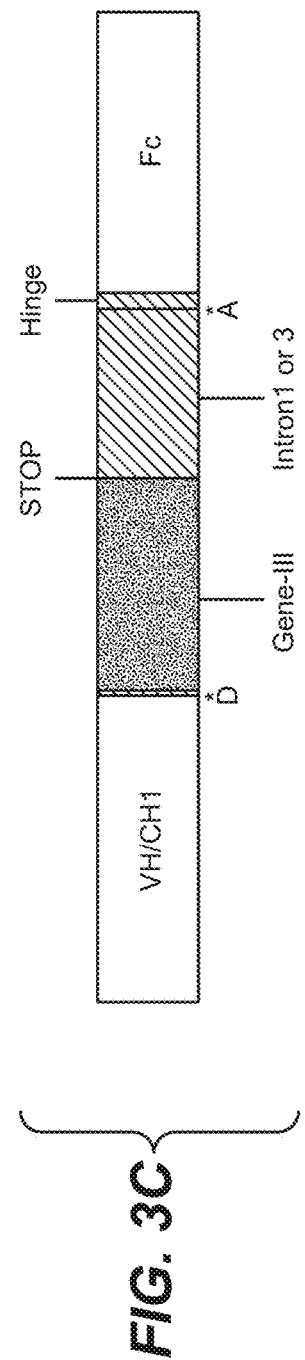
Figure 4A:
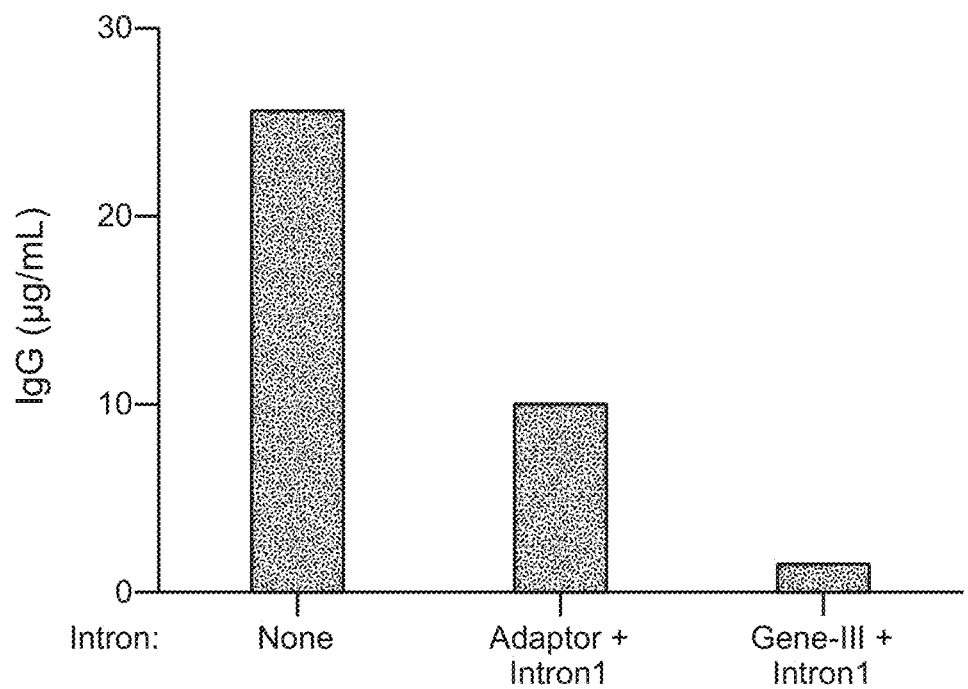
FIG. 4. (A) Expression levels of h4D5 IgG from constructs containing either no intron, a synthetic intron containing a phage adaptor peptide (See FIG. 3B), or a synthetic intron containing a phage coat protein (gene-III, see FIG. 3C). (B) RT-PCR of hIgG1 HC from transfected cells. The predicted size for a properly-spliced HC mRNA is 1,650 nt. The upper band in the adaptor+Intron1 construct represents an unspliced pre-cursor mRNA. The lower band in the adaptor- and gene-III-containing constructs is incorrectly spliced by a cryptic splice donor in the VH.
Figure 4B:
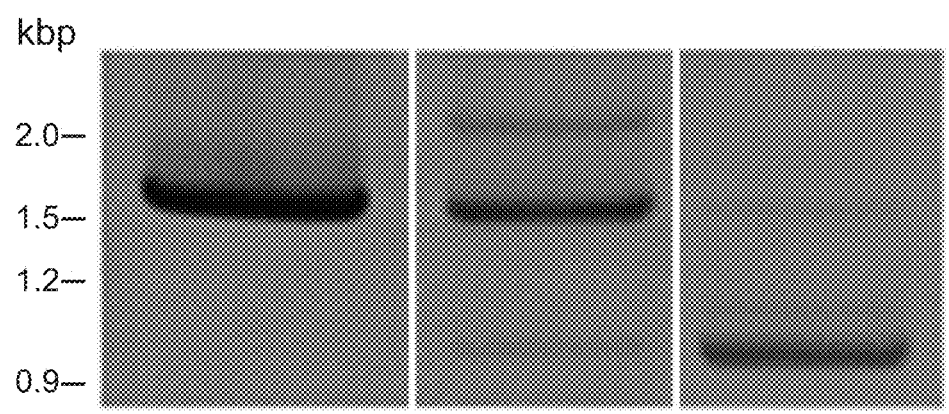

To determine whether the Fab fragment to a phage adaptor peptide embedded within the Intron1 sequence allows both display on phage and IgG expression in bacterial and mammalian cells, respectively, an adaptor peptide (FIG. 3B) or the phage coat protein gene-III (FIG. 3C) was inserted into the h4D5 HC.Intron1 construct at the 5' end of Intron 1 or Intron 3. The natural splice donor from Intron 1 or 3 was moved immediately upstream of the adaptor peptide. When the HC-adaptor.Intron1 construct was co-expressed with h4D5 LC in mammalian cells, the expression of h4D5 IgG was approximately 40% (for the adaptor-containing intron) or 5% (for the gene-III-containing intron) that of the control construct with no intron (FIG. 4A). RT-PCR demonstrated that, while a fraction of the HC-adaptor mRNA was properly spliced (FIG. 4B, middle band), a significant amount of the mRNA was either unspliced (FIG. 4B, upper band) or incorrectly spliced from a cryptic splice donor in the V$_H$ region (FIG. 4B, lower band). HC-gene-III mRNA was almost completely spliced from the cryptic splice donor. Silent mutation of the cryptic splice donor sequence resulted in accumulation of un-spliced mRNA only (not shown).

In light of the failure of the intron to efficiently splice when the adaptor sequence was inserted, we compared the sequence of the natural splice donor to the known consensus sequence of splice donors for mammalian mRNAs (Stephens et al., *J of Molecular Biology*, 228: 1124-1136 (1992)). As shown in FIG. 5, the natural splice donor from hIgG$_1$ Intron1 differs from the consensus donor sequence at three out of eight positions. Substitutions at positions 1 and 5 were analyzed further, as these positions are more conserved than position 8. A mutant splice donor (Donor1) in which the bases at positions 1 and 5 were changed to match the consensus sequence (FIG. 5A) was generated and tested the ability of these modified donors to mediate splicing of the synthetic intron in HC. This optimized splice donor completely restored splicing of the synthetic intron (FIG. 5B) with a concomitant increase in h4D5 IgG expression to a level that matched that of the control construct containing no intron (FIG. 5C). The improvement in splicing and IgG expression was observed whether the synthetic intron contains the adaptor peptide or gene-III and also whether the synthetic intron is based on the hIgG1 intron 1 or intron 3.

Example 3

Generation of Expression and Secretion System for Prokaryotic and Eukaryotic Cells For generation of the dual vector plasmid, we used the pBR322-derived phagemid vector currently used for phage display, pRS. This bi-cistronic vector consists of a bacterial PhoA promoter driving expression of an antibody light chain cassette with its associated STII signal sequence, followed antibody heavy chain cassette with its associated STII signal sequence. At the end of the light chain sequence, there is a gD epitope tag for detection of Fab display on phage particles. In conventional phagemids, the heavy chain sequence consists only of the $V_H$ and $C_H1$ domains of hIgG and is fused at the nucleotide level to a utility peptide, such as a phage fusion protein, most often gene-III, which encodes the phage coat protein pIII or an adaptor peptide. The 3' end of the light chain and heavy chain cassettes contain a lambda transcriptional terminator sequence for halting transcription in E. coli. Because this vector produces light chain and heavy chain-pIII from a single mRNA transcript, there are no transcriptional regulatory elements between the LC and HC sequences. The vector also contains the beta-lactamase (bla) gene to confer ampicillin resistance, the pMB1 origin for replication in E. coli, and f1 origin for expression of pillus on the bacterial surface, allowing for infection by M13 phage. Another form of this vector also includes the SV40 origin of replication for episomal replication of the plasmid in appropriate strains of mammalian cells.

For construction of the initial dual vector (referred to herein as "pDV.6.0"), we first inserted the mammalian CMV promoter from pRK (a mammalian expression vector used for expression of IgGs and other proteins) upstream of the PhoA promoter driving the LC-HC cistron. At the end of the LC antibody coding sequence, we inserted an Amber stop codon followed by a gD epitope tag, allowing detection of tagged LCs on phage when displayed in an Amber suppressor E. coli strain. The epitope tag is absent when the vector is expressed in mammalian cells. Thus, the LC cassette comprises (in order from 5' to 3') a eukaryotic promoter, a bacterial promoter, a signal sequence, an antibody light chain (LC) coding sequence, and an epitope tag (gD).

Next, between the HC and LC cassettes we inserted a synthetic cassette comprising of (in order from 5' to 3') an SV40 mammalian polyadenylation/transcriptional stop signal, a lambda terminator sequence for transcriptional termination in E. coli, a CMV promoter and a PhoA promoter.

Next, an SV40 mammalian polyadenylation/transcriptional stop signal and a lambda terminator sequence were inserted after the HC cassette. The HC cassette comprises a signal sequence and an antibody heavy chain (HC) coding sequence.

To allow for secretion of the fusion protein(s) of interest in both prokaryotic and eukaryotic cells, we replaced the STII signal sequences preceding the LC and HC with the eukaryotic murine binding immunoglobulin protein (mBiP) signal sequence. Screening of several candidate signal sequences lead us to discover that this signal sequence was capable of functioning in applications requiring prokaryotic expression (i.e., phage display) and/or eukaryotic expression (i.e., expression of IgG in mammalian cells), and that mBiP performed as well in both of these settings as did the respective signal sequences which were employed prior to this work.

To allow for expression of Fab-phage in E. coli and IgG in mammalian cells, we generated a synthetic intron in the HC cassette. We modified a natural intron from human IgG1 intron 1 or intron 3 to create a synthetic intron containing a fusion protein (gene-III) for display on phage particles. The genomic sequence of intron 1 (or intron 3) from human IgG1 was inserted immediately after the gene-III sequence separated by a stop codon to produce Fab HC-p3 fusions in E. coli. The placement of the natural splice donor octanucleotide at the 5' flanking region of the synthetic intron required two amino acid mutations in the hinge region when expressed in E. coli (E212G and P213K, Kabat numbering), and the mutations to create the optimized splice donor result in both of these residues being mutated to lysine. These mutations do not affect levels of display on phage (not shown) and, as the phage hinge region is removed during the splicing process, would be absent in the full-length IgG expressed in mammalian cells.

Alternatively, for utilization of adaptor phage display, we generated a vector similar to the pDV6.0 vector described above with a different synthetic intron (referred to herein as pDV5.0, shown in FIG. 7). The gene-III sequence was replaced with one of two members of a leucine zipper pair (herein called an "adaptor"). In this synthetic intron, the adaptor peptide sequence is followed by a stop codon and the genomic sequence of intron 1 or 3. In this construct, we also inserted a separate bacterial expression cassette consisting of gene-III fused to the cognate member of the leucine zipper pair. This separate bacterial expression cassette was introduced upstream of the LC CMV promoter and is controlled by a PhoA promoter, contains the STII signal sequence to restrict expression of the adaptor-gene-III to E. coli, and contains a lambda terminator immediately downstream. When expressed in E. coli, the heavy and light chains assemble in the periplasm to form Fab, and the adaptor fused to the heavy chain stably binds to the cognate adaptor on the pIII-adaptor protein. Packaging of this assembled Fab-adaptor-pIII complex into phage particles will yield phage displaying the Fab of interest. In addition, we generated a custom mutant of the KO7 helper phage in which the partner adaptor is fused to the N-terminus of gene-III (adaptor-KO7). Infection of E. coli harboring pDV.5.0 with adaptor-KO7 results in all copies of pIII present on the mature phagemid being fused to the adaptor. As a result, all copies of pIII are available to associate with Fab-adaptor, rather than only those copies of pIII that originated from pDV5. In some cases, however, a lower level of display may be desirable when rare high-affinity clones are sought (e.g., in affinity maturation applications). In this case, infection of E. coli harboring pDV.5.0 with conventional KO7 helper phage will result in a mixture of adaptor-pIII (from pDV.5.0) and wild-type pIII (from KO7 helper phage) being displayed on the phage particles. In this scenario, since only a subset of the overall pIII pool can associate with adaptor-Fab, the resulting display levels will be lower than when adaptor-KO7 is used. This ability to modulate display levels simply by choosing the appropriate helper phage is a unique advantage of the current invention.

Figure 6A:
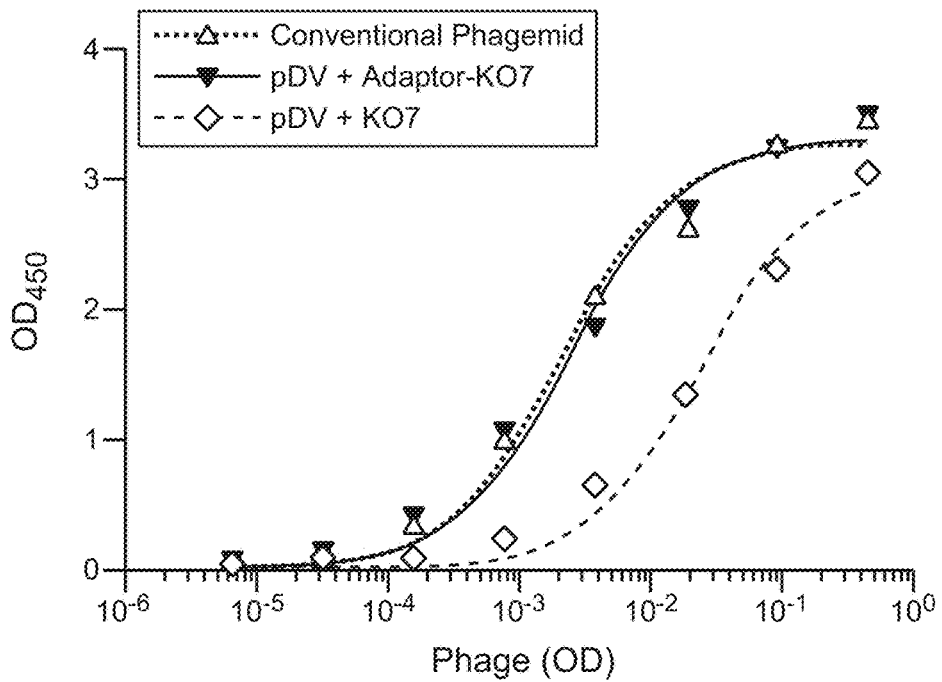
Figure 6B:
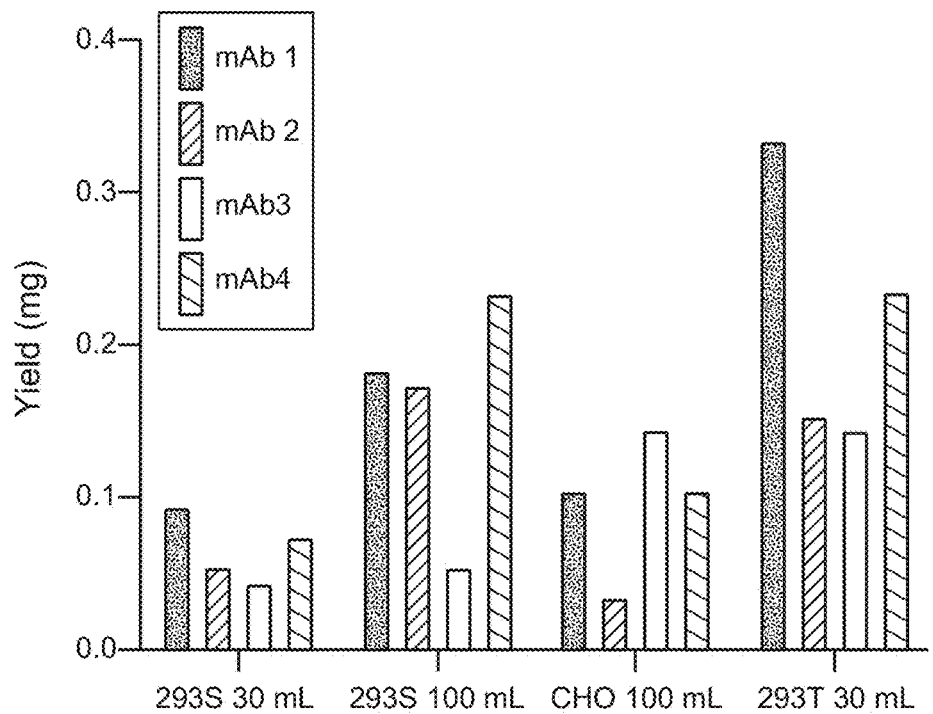

We evaluated the ability of pDV5.0 to express different IgGs in mammalian cells. The HCs and LCs from four different human IgGs were subcloned into pDV5.0 and expressed in 293 cells. Somewhat surprisingly, the overall yields from pDV were consistently ~10-fold lower than from a two-plasmid system. However, the yields are still on the order of ~0.1-0.4 mg per 30 mL culture (FIG. 6B). This amount of material is more than adequate for routine screening assays, and can easily be scaled up to 0.1-1 L or more if larger amounts of material are required. The IgGs were shown to be >90% monomeric in solution by gel filtration chromatography.

Example 4

Construction of Mutant Helper Phage, M13KO7 with Amber Mutation in Gene-III (AMBER KO7)

To enhance display of proteins fused to pIII on M13 phage, we generated a mutant helper phage, Amber KO7, using site-directed mutagenesis. Amber KO7 has an amber codon introduced in the M13KO7 helper phage genome by site-directed mutagenesis. The nucleotide sequence of the pIII (nucleotides 1579 to 2853 of mutant helper phage Amber KO7 is shown in FIG. 8.

To generate Amber KO7, helper phage M13KO7 was used to infect *Escherichia coli* CJ236 strain (genotype dut⁻/ung⁻) and progeny virions harvested to purifiy ssDNA using an ssDNA purification kit (QIAGEN). A synthetic oligonucleotide (sequence 5'-GTGAATTATCACCGTCAC-CGACCTAGGCCATTTGGGAATTAGAGCCA-3') (SEQ ID NO: 23) was used to mutate gene-III in M13KO7 by oligonucleotide-directed site mutagenesis. Mutagenized DNA was used to transform *E. coli* XL1-Blue cells (Agilent Technologies) and seeded on a lawn of uninfected XL1-Blue cells on soft agar plates. Plaques were individually picked and cells grown in LB media containing 50 μg/ml kanamycin. Double-stranded replicative form (RF) DNA was extracted with a DNA miniprep kit and sequenced to confirm the presence of the amber stop mutation. Homogeneity of population was confirmed by AvrII restriction endonuclease digestion and agar gel electrophoresis of RF DNA. All recombinant DNA manipulation steps were performed as described (Sambrook, J. et al., A Laboratory Manual, Third Edition, Cold Spring Harbor Laboratroy Press, Cold Spring Harbor, N.Y., 2001).

Figure 9:
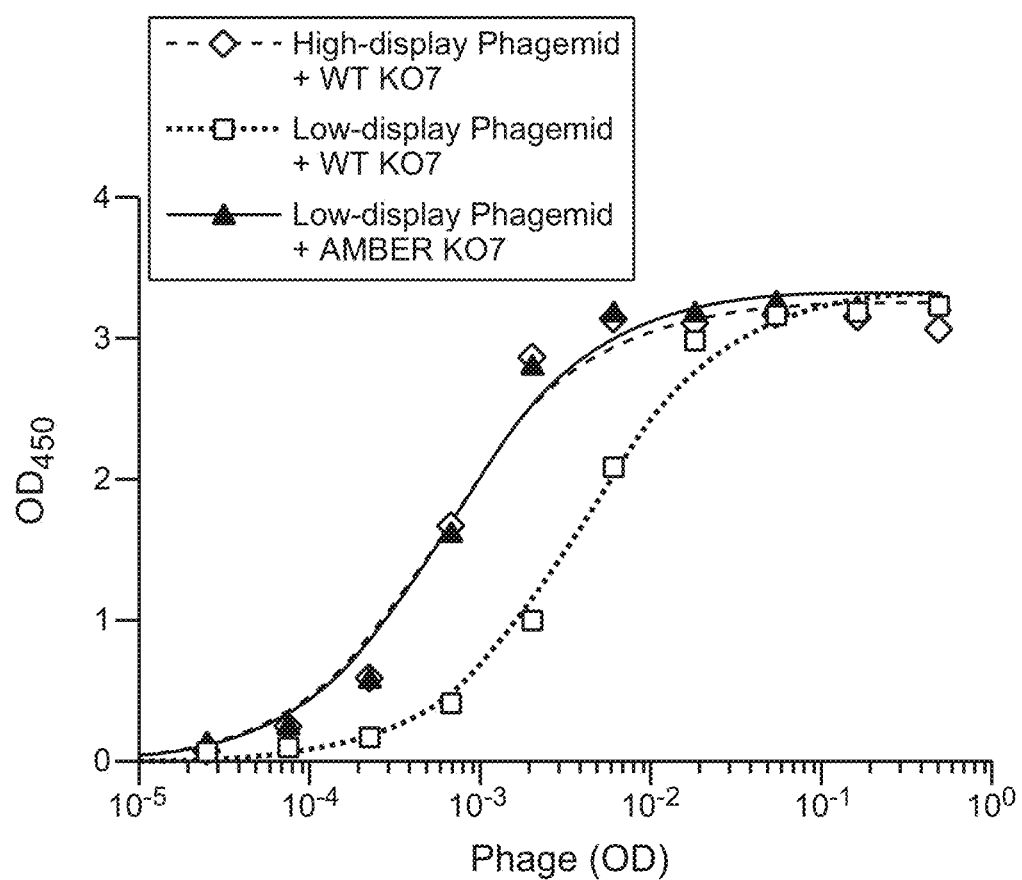
FIG. 9. Enhanced display of Fab fragments on pIII of M13 phage by use of Amber KO7 helper phage. A conventional high-display phagemid with wild-type M13KO7 (open diamonds) drives levels of Fab display significantly higher than those achieved by a low-display phagemid vector (closed squares) when wild-type M13KO7 is used for phage production. Use of a modified M13KO7 harboring an Amber mutation in pIII (Amber KO7) increases the display level of the low-display phagemid (closed triangles) to that of the high-display phagemid with wild-type M13KO7 (open diamonds).

The level of Fab display on phage particules produced using Amber KO7 was measured by phage ELISA. Antigen (Her2) was immobilized on immunoplates and phage bearing and anti-Her2 Fab were produced in XL1-Blue cells using either wild-type KO7 (WT KO7) or a modified M13KO7 harboring an Amber mutation in pIII (Amber KO7) helper phage. Binding was detected by incubating with a mouse anti-M13-HRP conjugate followed by TMB substrate OD measurement at 450 nm. The use of Amber KO7 resulted in higher display levels from a low-display phagemid (closed triangles) compared to the levels achieved by the same phagemid when WT KO7 was used for phage production (closed squares) (FIG. 9). The level of Fab display with the low-display phagemid using Amber KO7 (closed trianges) was also similar to the level of Fab display observed when using a high-display phagemid with WT KO7 (open diamonds) (FIG. 9).

Example 5

Generation of an Expression and Secretion System for Prokaryotic and Eukaryotic Cells for Generation of NaïVe HC-Only Libraries and Use of the System for Phage Panning In addition to the direct and indirect fusion vectors featuring prokaryotic and eukaryotic promoters on both HC and LC (pDV5.0 and pDV6.0) described in Example 3, we generated a modified direct fusion dual vector construct (pDV.6.5 shown in FIG. 14) in which the Fab LC is fused to the STII signal sequence and is driven only by a bacterial PhoA promoter whereas the Fab HC (containing the gene-III-synthetic intron and hIgG Fc sequences for expression of a full-length hIgG1 HC in mammalian cells) was driven by both a eukaryotic CMV promoter and a prokaryotic PhoA promoter. This construct was used to recapitulate a synthetic human Fab library previously described (Lee, et al., *Journal of Molecular Biology*, 340. 1073-1093 (2004)), in which diversity is introduced into the HC only. Expression of full-length IgG from this vector requires cotransfection of a mammalian expression vector which encodes a LC.

Phage-displayed libraries were generated using oligo-nucleotide-directed (Kunkel) mutagenesis and "stop template" versions of pDV.6.5 in which stop codons (TAA) were placed into all three heavy-chain CDRs. These stops were repaired during the mutagenesis reaction by a mixture of oligonucleotides that annealed over the regions encoding CDRH1, H2 and H3 and replaced codons at the positions chosen for randomization with degenerate codons. Mutagenesis reactions were electroporated into XL1-Blue cells, and the cultures were grown using a temperature shift protocol (37° C. for 4 hours followed by 36 hours at 30° C.) in 2YT broth supplemented with Amber.KO7 helper phage, 50 μg/ml carbenicillin and 25 μg/ml kanamycin. Phage were harvested from the culture medium by precipitation with PEG/NaCl. Each electroporation reaction used ~5 μg of DNA and resulted in $1 \times 10^8 - 7 \times 10^8$ transformants.

Figure 10:
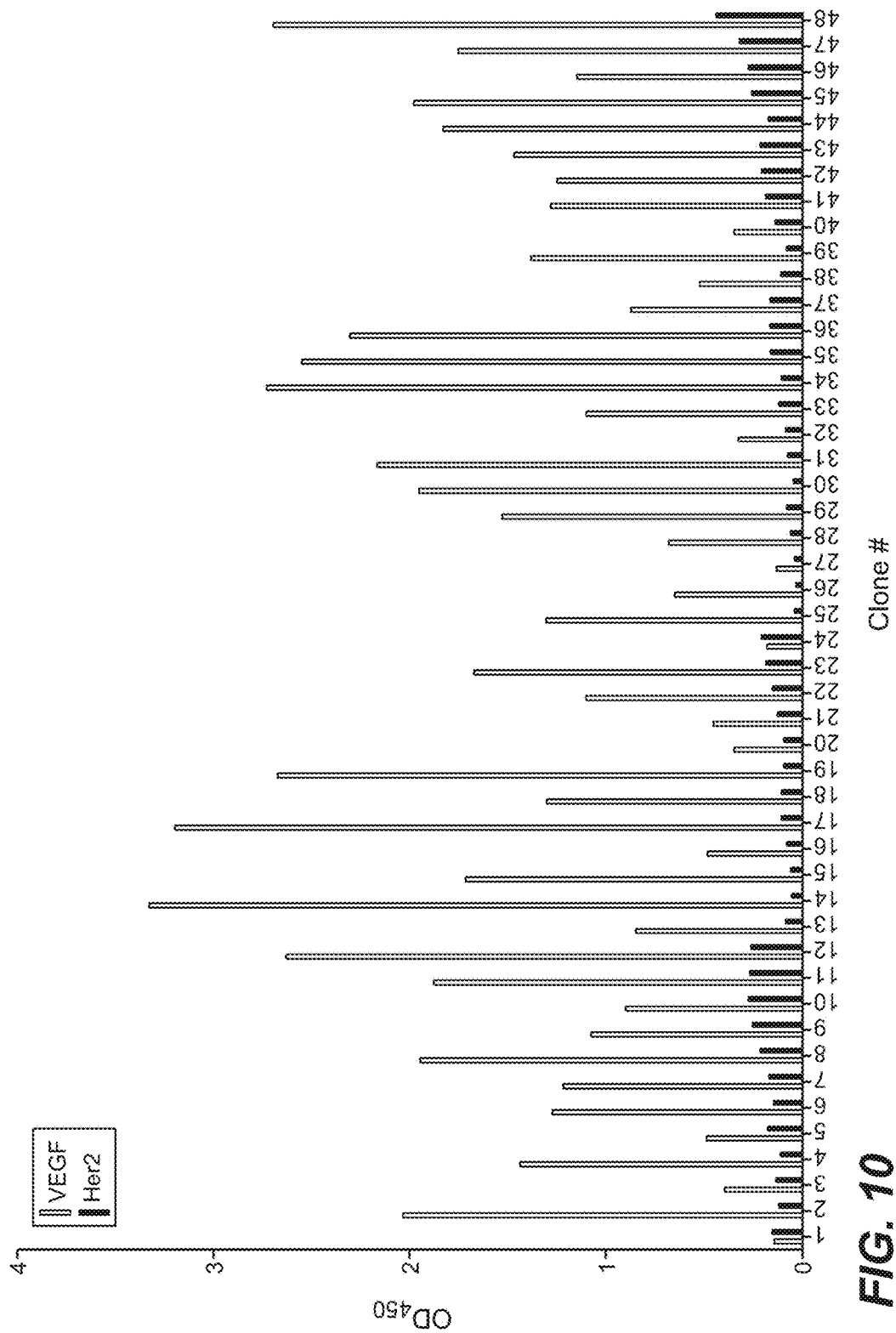
FIG. 10 is a bar graph which shows the binding (as measured by phage ELISA) of clones selected from phage library sorting of a naïve dual vector Fab-phage library of Example 5 against immobilized VEGF. Individual clones were picked after four rounds of selection and phage supernatants were tested for binding to immobilized antigen (VEGF) and to an irrelevant protein (Her2) to evaluate binding specificity.

Panning of a naïve phage library generated in this vector was performed against the human vascular endothelial growth factor (VEGF). For phage library sorting, protein antigens were immobilized on Maxisorp immunoplates and libraries were subjected to four to five rounds of binding selections. Wells were blocked alternatively using BSA or casein in alternating rounds. Random clones selected from rounds 3 through 5 were assayed using a phage ELISA to compare binding to target antigen (VEGF) and an irrelevant protein (Her2) for checking non-specific binding. Briefly, phage clones were grown overnight in 1.6 mL of 2YT broth supplemented with Amber.KO7 helper phage (Example 4). Supernatants were bound to immobilized antigen or irrelevant protein-coated plates for 1 hour at room temperature. After washing, bound phage was detected using an HRP-conjugated anti-M13 antibody (20 minutes at room temperature) followed by detection with TMB substrate. We isolated multiple clones which were ELISA positive for VEGF, but not for an irrelevant control protein (Her2) (FIG. 10—bar graph).

DNA from these clones that demonstrated specificity for VEGF was then used to express full-length IgG by con-transfection with a mammalian expression vector encoding the common LC in 293 cells in small scale suspension cultures for expression of full-length hIgG1. 1 mL cultures were transfected using Expifectamine or JetPEI according to the manufacturer's instructions and incubated at 37 degrees C./8% $CO_2$ for 5-7 days. Scaled-up transfections were performed in 30 mL 293 cells.

Figure 11:
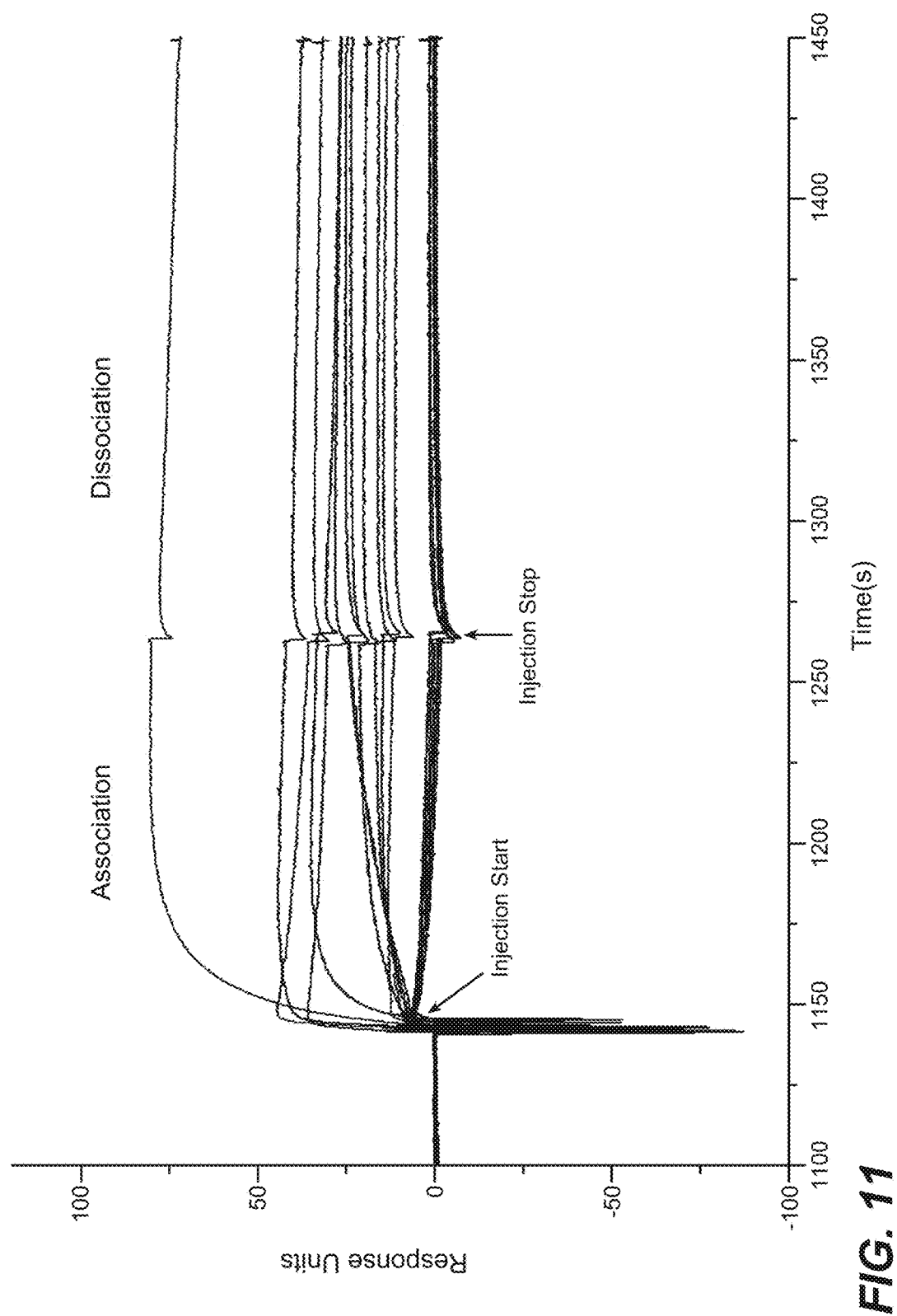
FIG. 11 shows screening of selected phage clones in IgG format by BIAcore for antigen binding to VEGF, as measured by an Fc-capture assay on a BIAcore T100 instrument. The 96 clones that were picked for sequence analysis analysis and phage ELISA were transfected into 293S cells (1 mL) and cultured for seven days for IgG expression. Supernatants were 0.2 µm filtered and used to evaluate VEGF antigen binding by an Fc-capture assay on a BIAcore T100 instrument.

Culture supernatants were then used to screen the IgGs for VEGF binding in an Fc capture assay on a BIAcore T100 instrument (FIG. 11). IgG supernatants from 1 mL cultures were used to screen for antigen binding. An anti-human Fc capture antibody was immobilized onto a series S CM5 sensor chip (~10,000 RU). Supernatants were sequentially flowed over flow cells 2, 3 and 4 (5 μL/min for 4 minutes) to allow capture of IgG from the supernatant (50-150 RU), after which antigen (100-1000 nM) was flowed over the immobilized IgGs (30 μL/min for 2 minutes) to measure the binding response.

Sequencing of the positive binders show eight unique sequences (heavy chain CDR sequences are shown in FIG. 12) with positive binding properties (FIG. 12). The sequencing data (FIG. 12) combined with the phage ELISA (FIG. 10) and BiaCore data (FIG. 11) was used to select a pool of eight anti-VEGF clones for further analysis. Expression for these eight clones was scaled up to 100 mL chinese hamster overay (CHO) cell cultures (see FIG. 15) and purified material was used to evaluate the ability of the anti-VEGF clones to block the binding of VEGF to one of its cognate receptors (VEGFR1) via a receptor-blocking ELISA. Biotinylated hVEGF165 (2 nM) was incubated with 3-fold serially diluted anti-VEGF antibodies (200 nM top concentration) in PBS/0.5% BSA/

0.05% Tween-20. After 1-2 hours of incubation at room temperature, the mixtures were transferred to the VEGFR1-immobilized plate and incubated for 15 minutes. VEGFR-1 bound VEGF was then detected by streptavidin-HRP for 30 minutes followed by development with TMB substrate and the IC50 value was measured.

Figure 13:
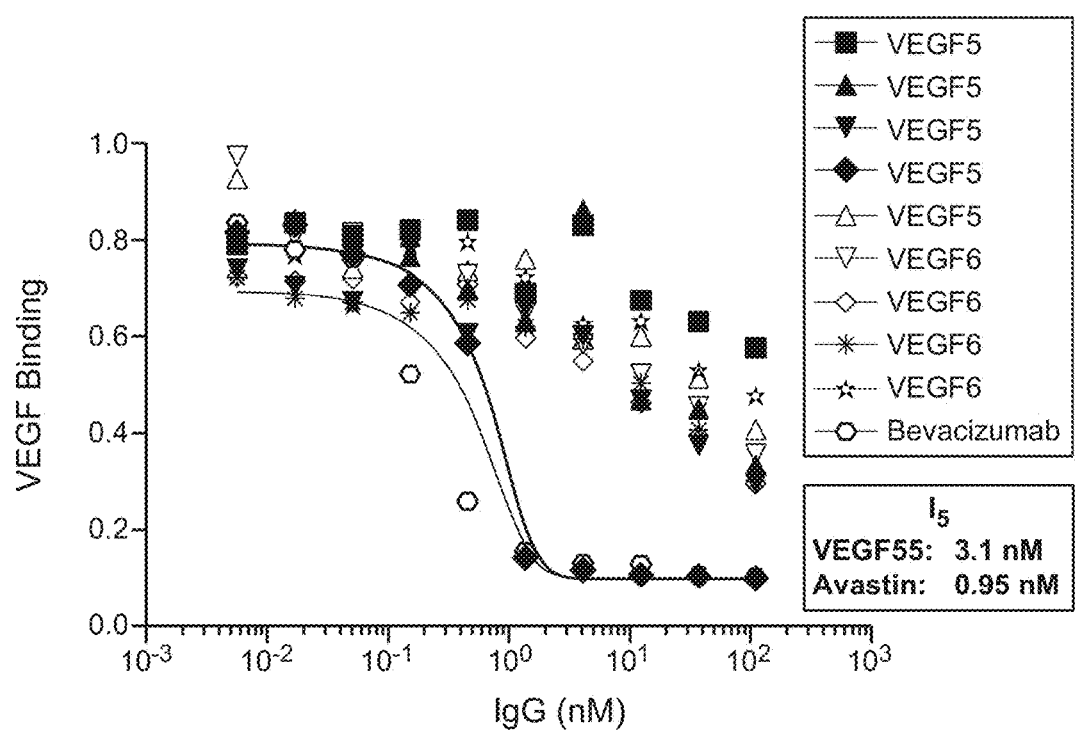
FIG. 13 shows the ability of selected anti-VEGF IgGs selected from phage sorting against VEGF to inhibit binding of VEGF to one of its natural receptors, VEGF-R1. Selected antibodies from sorting against VEGF were expressed in CHO cells and purified IgG was used to measure the capacity of the selected clones to inhibit binding of VEGF to VEGF-R1. One clone (VEGF55) inhibited VEGF-R1 binding with an IC50 that was within 3.5-fold of bevacizumab (Avastin).

We identified one clone (VEGF55) with an $IC_{50}$ comparable to that of bevicizumab, a commercial anti-VEGF antibody (FIG. 13). In this way, we were able to move directly from phage panning to IgG exression and triage a pool of clones down to a single candidate, all without the requirement to subclone.

In summary, this modified direct fusion dual vector (pDV.6.5) was able to be used for the construction of phage display libraries with randomized heavy chains and constant light chains in E. coli and was also able to be used to subsequently express selected clones as native IgG1 in mammalian cells without subcloning when complemented with a light chain expression vector. Because the mammalian CMV promoter is present upstream of HC only, pDV expressed both Fab LC and Fab HC-pIII in E. coli, but expressed only hIgG1HC in mammalian cells. This vector was used to select Fab fragments from a naïve synthetic Fab library binding multiple antigens, and then to express full-length native hIgG1 from the selected clones in mammalian 293 and CHO cells by cotransfecting the modified direct fusion dual vector clones with a mammalian expression vector encoding a common LC. Native IgG1 was obtained from these expression experiments to conduct several assays, such that from a pool of 8 unique anti-VEGF clones showing binding activity by ELISA and BIAcore, we were able to triage down to a single candidate bo evaluating in-solution behavior, non-specific binding, and biologica activity of the candidates in IgG format without the need to sublone HC sequences from the original phage vector clones.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated nucleic acid molecule encoding a first polypeptide, a second polypeptide, a signal sequence, and a coat protein or adaptor protein, wherein:
   (a) the first polypeptide comprises a variable light chain (VL) domain comprising a VL-HVR1, a VL-HVR2, and a VL-HVR3;
   (b) the second polypeptide comprises a variable heavy chain (VH) domain comprising a VH-HVR1, a VH-HVR2, and a VH-VHR3;
   (c) the signal sequence is functional in both a prokaryotic cell and an eukaryotic cell and is encoded by a nucleic acid sequence that is 5' to the nucleic acid sequence encoding the first polypeptide and 5' to the nucleic acid sequence encoding the second polypeptide, wherein the signal sequence is encoded by a nucleic acid sequence selected from the group consisting of SEQ ID NO: 11 (consensus mBIP sequence, X ATG AAN TTN ACN GTN GTN GCN GCN GCN CTN CTN CTN CTN GGN GCN GTN CGN GCN, wherein N=A, T, C or G, and wherein X =ATG, X=ATG ACC or X is absent), SEQ ID NO: 16 (Opt1, ATG ATG AAA TTT ACC GTT GTT GCT GCT GCT CTG CTA CTT CTT GGA GCG GTC CGC GCA), SEQ ID NO: 17 (Opt2, ATG ATG AAA TTT ACT GTT GTT GCG GCT GCT CTT CTC CTT CTT GGA GCG GTC CGC GCA), or SEQ ID NO: 18 (Opt 3, ATG ATG AAA TTT ACT GTT GTC GCT GCT GCT CTT CTA CTT CTT GGA GCG GTC CGC GCA); and
   (d) the first polypeptide and the second polypeptide form a full-length antibody wherein the first and/or second polypeptide is fused to a coat protein or an adaptor protein.

2. The nucleic acid molecule of claim 1, wherein the nucleic acid sequence encoding the signal sequence is operably linked to the 5' end of the nucleic acid sequence encoding the first polypeptide and the 5' end of the nucleic acid sequence encoding the second polypeptide.

3. The nucleic acid molecule of claim 1, wherein the VL domain and the VH domain are each linked to a utility peptide.

4. The nucleic acid molecule of claim 3, wherein the VH domain is linked to a CH1 domain and the VL domain is linked to a CL domain.

5. The nucleic acid molecule of claim 4, wherein the utility peptide is selected from the group consisting of a Fc, a tag, a label, and a control protein.

6. The nucleic acid molecule of claim 5, wherein the VL domain is linked to a control protein and the VH domain is linked to the Fc.

7. The nucleic acid molecule of claim 6, wherein the control protein is a gD protein, or a fragment thereof.

8. The nucleic acid molecule of claim 1, wherein the nucleic acid encoding the first polypeptide or the second polypeptide is fused to a synthetic intron, wherein the synthetic intron comprises a nucleic acid encoding the coat protein or adaptor protein.

9. The nucleic acid molecule of claim 8, wherein the synthetic intron is located between a nucleic acid encoding a VH domain and a nucleic acid encoding an Fc or a hinge.

10. The nucleic acid molecule of claim 9, wherein the synthetic intron further comprises a nucleic acid encoding a naturally occurring intron of IgG1.

11. The nucleic acid molecule of claim 10, wherein the naturally occurring intron is selected from the group consisting of intron 1, intron 2, and intron 3 of IgG1.

12. The nucleic acid molecule of claim 11, wherein the naturally occurring intron is intron 1 of IgG1.

13. The nucleic acid molecule of claim 8, wherein the nucleic acid encodes an adaptor protein, and wherein the adaptor protein is a leucine zipper.

14. The nucleic acid molecule of claim 8, wherein the nucleic acid encodes an adaptor protein, and wherein the adaptor protein comprises the amino acid sequence of SEQ ID NO: 8, 9, 12, 13, 14 or 15.

15. The nucleic acid molecule of claim 8, wherein the nucleic acid encodes a coat protein, and wherein the coat protein is selected from the group consisting of pI, pII, pIII, pIV, pV, pVI, pVII, pVIII, pIX, and pX of bacteriophage M13, f1, or fd.

16. The nucleic acid molecule of claim 15, wherein the coat protein is pIII, or a fragment thereof.

17. The nucleic acid molecule of claim 16, wherein the pIII fragment is amino acids 267-421 or 262-418 of the pIII protein.

18. The nucleic acid molecule of claim 15, wherein a first fab fusion protein is expressed in prokaryotic cells and a second fab fusion protein is expressed in eukaryotic cells.

19. The nucleic acid molecule of claim 18, wherein the first fab fusion protein and the second fab fusion protein are the same.

20. The nucleic acid molecule of claim 18, wherein the first fab fusion protein and the second fab fusion protein are different.

21. The nucleic acid molecule of claim 20, wherein the first fab fusion protein is a Fab-phage fusion protein.

22. The nucleic acid molecule of claim 21, wherein the Fab-phage fusion protein comprises VH/CH1 fused to the pIII.

23. The nucleic acid molecule of claim 22, wherein the second fusion is a Fab-Fc or a Fab-hinge-Fc fusion protein.

24. The nucleic acid molecule of claim 23, wherein the Fab-Fc or the Fab-hinge-Fc fusion protein comprises VH/CH1 fused to Fc.

25. The nucleic acid molecule of claim 4, wherein the CH1 domain comprises a portion of a natural splice donor sequence.

26. The nucleic acid molecule of claim 5, wherein the Fc comprises a portion of a natural splice acceptor sequence.

27. The nucleic acid molecule of claim 4, wherein the CH1 domain comprises a portion of a splice donor sequence, wherein the portion of the splice donor sequence comprises a modification of at least one nucleic acid residue, and wherein the modification increases splicing efficiency of the nucleic acid molecule relative to a control construct comprising an unmodified splice donor sequence.

28. The nucleic acid molecule of claim 8, wherein the nucleic acid encodes an adaptor protein, and wherein the adaptor protein comprises an amino acid sequence of SEQ ID NO: 6 (ASIARLRERVKTLRARNYELRSRANMLR-ERVAQLGGC) or SEQ ID NO: 7 (ASLDELE-AEIEQLEEENYALEKEIEDLEKELEKLGGC).

29. A vector comprising the nucleic acid molecule of claim 1.

30. A cultured host cell transformed with the vector of claim 29.

31. The cultured host cell of claim 30 wherein the cultured host cell is a bacteria cell.

32. The cultured host cell of claim 31, wherein the bacteria cell is an *E. coli* cell.

33. The cultured host cell of claim 30, wherein the cultured host cell is a eukaryotic cell.

34. The cultured host cell of claim 33, wherein the eukaryotic cell is a yeast cell, a CHO cell, a 293 cell, or a NSO cell.

35. A process for producing an antibody comprising culturing the cultured host cell of claim 30, wherein the antibody is expressed.

36. The process of claim 35, further comprising recovering the antibody expressed by the cultured host cell.

37. The process of claim 36, wherein the antibody is recovered from the cultured host cell culture medium.

38. The nucleic acid molecule of claim 8, wherein the synthetic intron is located between a nucleic acid encoding a CH2 domain and a CH3 domain of the antibody.

39. The nucleic acid molecule of claim 8, wherein the synthetic intron is located between a nucleic acid encoding a hinge region and a CH2 domain of the antibody.

* * * * *

UNITED STATES PATENT AND TRADEMARK OFFICE
CERTIFICATE OF CORRECTION

PATENT NO. : 9,803,191 B2
APPLICATION NO. : 13/934570
DATED : October 31, 2017
INVENTOR(S) : Devin Tesar et al.

Page 1 of 2

It is certified that error appears in the above-identified patent and that said Letters Patent is hereby corrected as shown below:

On the Title Page

Under OTHER PUBLICATIONS, in Johansson et al., replace "31 8:37-46" with --318:37-46--;
In Kramer et al., replace "Res. 11311(11):e59" with --Res. 31(11):e59--.

In the Specification

Column 3, Line 59, replace "may selected from" with --may be selected from--.

Column 4, Line 37, replace "GCN). or by a" with --GCN), or by a--.

Column 5, Line 31, replace "prokyarotic" with --prokaryotic--.

Column 6, Line 31, replace "intron1" with --intron 1--;
Line 33, replace "intron1" with --intron 1--;
Line 36, replace "intron1" with --intron 1--;
Line 37, replace "intron1" with --intron 1--;
Line 39, replace "intron1" with --intron 1--;
Line 48, replace "intron1" with --intron 1--;
Line 53, replace "intron1" with --intron 1--;
Line 53, replace "donor to increases" with --donor increases--;
Line 58, replace "no intron present" with --no intron present.--.

Column 7, Lines 44-45, replace "sequence analysis analysis and" with --sequence analysis and--.

Column 13, Line 53, replace "(HVR5)" with --(HVRs)--.

Column 15, Line 53, replace "and a single signal sequences drives" with --and a single signal sequence drives--.

Signed and Sealed this
Thirty-first Day of July, 2018

Andrei Iancu
*Director of the United States Patent and Trademark Office*

CERTIFICATE OF CORRECTION (continued)
U.S. Pat. No. 9,803,191 B2

Column 16, Line 39, replace "concensus" with --consensus--.

Column 17, Line 20, replace "protein ro an adaptor" with --protein or an adaptor--;
    Line 22, replace "natural plice donor" with --natural splice donor--;
    Line 24, replace "Other examples, include" with --Other examples include--.

Column 18, Line 21, replace "lable" with --label--.

Column 19, Line 3, replace "100 μM or 26 μM" with --100 pM or 26 pM--;
    Line 51, replace "spectrophometer" with --spectrophotometer--.

Column 31, Line 36, replace "2935 cells" with --293S cells--.

Column 35, Line 24, replace "phage particules" with --phage particles--;
    Line 38, replace "(closed trianges)" with --(closed triangles)--.

Column 36, Line 61, replace "chinese hamster overay" with --Chinese hamster ovary--.

Column 38, Line 11, replace "single candidate bo evaluating" with --single candidate by evaluating--;
    Lines 12-13, replace "biologica activity" with --biological activity--;
    Line 14, replace "sublone" with --subclone--.

In the Claims

Column 67, Line 10, Claim 1, under (b), replace "VHR3" with --HVR3--;
    Line 32, Claim 1, under (d), replace "a full-length antibody wherein" with --a full-length antibody; wherein--;
    Line 67, Claim 11, replace "intron 3of IgG1." with --intron 3 of IgG1--.

Column 68, Line 22, Claim 18, replace "fab fusion" with --Fab fusion--;
    Line 23, Claim 18, replace "fab fusion" with --Fab fusion--;
    Line 25, Claim 19, replace "fab fusion protein and the second fab fusion protein" with --Fab fusion protein and the second Fab fusion protein--;
    Line 28, Claim 20, replace "first fab fusion and second fab fusion" with --first Fab fusion and second Fab fusion--;
    Line 31, Claim 21, replace "fab fusion" with --Fab fusion--;
    Line 62, Claim 31, replace "claim 30 wherein" with --claim 30, wherein--;
    Line 65, Claim 32, replace "*E. coli*cell" with --*E. coli* cell--.